US007959860B2

(12) United States Patent
Faries, Jr. et al.

(10) Patent No.: US 7,959,860 B2
(45) **Date of Patent: *Jun. 14, 2011**

(54) SYSTEM AND METHOD OF DETECTING FLUID AND LEAKS IN THERMAL TREATMENT SYSTEM BASINS

(76) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

( * ) Notice: Subject to any disclaimer, the term of this patent is extended or adjusted under 35 U.S.C. 154(b) by 1195 days.

This patent is subject to a terminal disclaimer.

(21) Appl. No.: 11/350,363

(22) Filed: Feb. 9, 2006

(65) Prior Publication Data

US 2006/0194324 A1 Aug. 31, 2006

Related U.S. Application Data

(63) Continuation-in-part of application No. 10/836,236, filed on May 3, 2004, now Pat. No. 7,347,210, which is a continuation-in-part of application No. 10/372,674, filed on Feb. 25, 2003, now Pat. No. 6,910,485, which is a continuation-in-part of application No. 10/172,731, filed on Jun. 17, 2002, now Pat. No. 7,176,030, which is a continuation-in-part of application No. 09/983,021, filed on Oct. 22, 2001, now Pat. No. 6,810,881.

(60) Provisional application No. 60/467,129, filed on May 2, 2003.

(51) Int. Cl.
*A61L 2/24* (2006.01)

(52) U.S. Cl. ................ 422/62; 422/3; 422/105; 422/40; 422/119; 422/41; 62/66; 62/68; 62/72; 62/342; 128/849; 128/897

(58) Field of Classification Search ........................ None
See application file for complete search history.

(56) References Cited

U.S. PATENT DOCUMENTS 2,599,192 A 6/1952 Miller
2,613,511 A 10/1952 Walsh
2,807,701 A 9/1957 Conlin et al.
3,807,954 A 4/1974 McDonald
3,869,596 A 3/1975 Howie
3,902,484 A 9/1975 Winters
4,053,954 A 10/1977 Chapman
4,270,067 A 5/1981 Thomas et al.
4,284,880 A 8/1981 Keiser
4,393,659 A 7/1983 Keyes et al.
4,458,139 A 7/1984 McClean (Continued)

*Primary Examiner* — Sally A Sakelaris
(74) *Attorney, Agent, or Firm* — Edell, Shapiro & Finnan, LLC

(57) ABSTRACT

A drape including a sensing device according to the present invention is disposed over a top surface of a thermal treatment system having a basin recessed therein. A portion of the drape is pushed down into the basin to form a drape container for collecting a sterile medium. The thermal treatment system may be of the type that either heats or congeals the sterile medium. The sensing device includes electrodes that are typically disposed through the drape and sealed. The electrodes provide signals indicating the presence of liquid and/or leaks or other conditions within the drape container to the system to facilitate control of system operation. In addition, the sensing device includes a fuse to limit the drape to a single use. The system disables the fuse to indicate prior use and detects tampering to bypass the fuse, thereby preventing use of the drape for subsequent medical procedures.

76 Claims, 12 Drawing Sheets

U.S. PATENT DOCUMENTS 4,474,016 A 10/1984 Winchell
4,522,041 A 6/1985 Menzel
4,625,098 A 11/1986 Joe
4,782,835 A 11/1988 Bernardini
4,828,876 A 5/1989 Ohhara et al.
4,869,271 A 9/1989 Idris
4,903,710 A 2/1990 Jessamine et al.
4,934,152 A 6/1990 Templeton
4,967,061 A 10/1990 Weber, Jr. et al.
5,040,699 A 8/1991 Gangemi
5,042,455 A 8/1991 Yue et al.
5,042,981 A 8/1991 Gross
5,129,033 A 7/1992 Ferrara et al.
5,163,299 A 11/1992 Faries, Jr. et al.
5,174,306 A 12/1992 Marshall
5,310,524 A 5/1994 Campbell et al.
5,331,820 A 7/1994 Faries, Jr. et al.
5,333,326 A 8/1994 Faries, Jr. et al.
5,345,063 A 9/1994 Reusche et al.
5,351,675 A 10/1994 Brodsky
5,363,746 A 11/1994 Gordon
5,374,813 A 12/1994 Shipp
5,383,476 A 1/1995 Peimer et al.
5,386,835 A 2/1995 Elphick et al.
5,396,905 A 3/1995 Newman et al.
5,400,267 A 3/1995 Denen et al.
5,400,616 A 3/1995 Faries, Jr. et al.
5,402,644 A 4/1995 Faries, Jr. et al.
5,429,801 A 7/1995 Faries, Jr. et al.
5,435,322 A 7/1995 Marshall
5,443,082 A 8/1995 Mewburn
5,449,892 A 9/1995 Yamada
5,457,962 A 10/1995 Faries, Jr. et al.
5,463,213 A 10/1995 Honda
5,480,302 A 1/1996 Fife
5,502,980 A 4/1996 Faries, Jr. et al.
5,517,170 A 5/1996 Peters et al.
5,522,095 A 6/1996 Faries, Jr. et al.
5,522,805 A 6/1996 Vancaillie et al.
5,524,478 A 6/1996 Joy et al.
5,524,643 A 6/1996 Faries, Jr. et al.
5,531,697 A 7/1996 Olsen
5,539,185 A 7/1996 Polster
5,549,543 A 8/1996 Kim
5,551,240 A 9/1996 Faries, Jr. et al.
5,615,423 A 4/1997 Faries, Jr. et al.
5,653,938 A 8/1997 Faries, Jr. et al.
5,658,478 A 8/1997 Roeschel et al.
5,664,582 A 9/1997 Szymaitis
5,715,547 A 2/1998 Becker et al.
5,717,188 A 2/1998 Vaillancourt
5,800,352 A 9/1998 Ferre et al.
5,809,788 A 9/1998 Faries, Jr. et al.
5,816,252 A 10/1998 Faries, Jr. et al.
5,857,467 A 1/1999 Faries, Jr. et al.
5,862,672 A 1/1999 Faries, Jr. et al.
5,879,621 A * 3/1999 Faries et al. ........................ 422/3
5,950,438 A 9/1999 Faries, Jr. et al.
6,003,328 A 12/1999 Faries, Jr. et al.
6,035,855 A 3/2000 Faries, Jr. et al.
6,087,636 A 7/2000 Faries, Jr. et al.
6,091,058 A * 7/2000 Faries et al. ................... 219/430
6,102,044 A 8/2000 Naidyhorski
6,255,627 B1 7/2001 Faries, Jr. et al.
6,259,067 B1 * 7/2001 Faries et al. ................... 219/428
6,341,704 B1 1/2002 Michel, Jr.
6,371,121 B1 * 4/2002 Faries et al. ................... 128/849
6,448,571 B1 9/2002 Goldstein
6,586,950 B1 7/2003 Sargent et al.
6,593,552 B1 7/2003 Li
6,701,174 B1 3/2004 Krause et al.
6,810,881 B2 * 11/2004 Faries et al. ................... 128/849
6,860,271 B2 3/2005 Faries, Jr. et al.
6,884,970 B2 4/2005 Lehman
6,910,485 B2 6/2005 Faries, Jr. et al.
6,918,395 B2 7/2005 Faries, Jr. et al.
6,927,365 B2 8/2005 Li
7,041,941 B2 5/2006 Faries, Jr. et al.
7,176,030 B2 2/2007 Faries, Jr. et al.
7,276,675 B2 10/2007 Faries, Jr. et al.
7,307,245 B2 12/2007 Faries, Jr. et al.
7,309,472 B2 12/2007 Michaelson et al.
7,311,660 B2 12/2007 Gomez
7,347,210 B2 * 3/2008 Faries et al. ................... 128/849
7,350,373 B1 4/2008 Faries, Jr. et al.
7,417,205 B2 8/2008 Faries, Jr. et al.
7,418,966 B2 * 9/2008 Faries et al. ................... 128/849
7,671,302 B1 3/2010 Faries, Jr. et al.
7,728,262 B1 6/2010 Faries, Jr. et al.
2003/0132216 A1 7/2003 Li
2003/0231990 A1 12/2003 Faries, Jr. et al.
2004/0200480 A1 10/2004 Faries, Jr. et al.
2004/0200483 A1 10/2004 Faries, Jr. et al.
2004/0208780 A1 * 10/2004 Faries et al. ........................ 422/3
2005/0247169 A1 11/2005 Faries, Jr. et al.
2006/0065276 A1 3/2006 Kammer et al.
2006/0086361 A1 4/2006 Kammer et al.
2006/0091128 A1 5/2006 Kammer et al.
2006/0091129 A1 5/2006 Colonna
2006/0260443 A1 11/2006 Faries, Jr. et al.
2006/0289445 A1 12/2006 Colonna
2007/0089753 A1 4/2007 Faries, Jr. et al.
2009/0255540 A1 10/2009 Faries, Jr.
2010/0116810 A1 5/2010 Faries, Jr. et al.
2010/0200561 A1 8/2010 Faries, Jr. et al.

* cited by examiner

SYSTEM AND METHOD OF DETECTING FLUID AND LEAKS IN THERMAL TREATMENT SYSTEM BASINS

CROSS-REFERENCE TO RELATED APPLICATIONS

This application is: a continuation-in-part of U.S. patent application Ser. No. 10/172,731, entitled "Method and Apparatus for Ensuring Sterility of Disposable Medical Items Used with Medical Equipment" and filed Jun. 17, 2002; now U.S. Pat. No. 7,176,030 and a continuation-in-part of U.S. patent application Ser. No. 10/836,236, entitled "Surgical Drape with Conductor and Method of Detecting Fluid and Leaks in Thermal Treatment System Basins" and filed May 3, 2004, now U.S. Pat. No. 7,347,210 which is a continuation-in-part of U.S. patent application Ser. No. 10/372,674, entitled "Medical Solution Thermal Treatment System and Method of Controlling System Operation in Accordance with Detection of Solution and Leaks in Surgical Drape Containers" and filed Feb. 25, 2003, now U.S. Pat. No. 6,910,485, which is a continuation-in-part of U.S. patent application Ser. No. 09/983,021, entitled "Medical Solution Thermal Treatment System and Method of Controlling System Operation in Accordance with Detection of Solution and Leaks in Surgical Drape Containers" and filed Oct. 22, 2001, now U.S. Pat. No. 6,810,881. In addition, aforementioned U.S. patent application Ser. No. 10/836,236 claims priority from U.S. Provisional Patent Application Ser. No. 60/467,129, entitled "Surgical Drape with Conductor and Method of Detecting Fluid and Leaks in Thermal Treatment System Basins" and filed May 2, 2003. The disclosures of the aforementioned patents and patent applications are incorporated herein by reference in their entireties.

BACKGROUND OF THE INVENTION

1. Technical Field

The present invention pertains to thermal treatment systems. In particular, the present invention pertains to detection of the presence of solution and/or leaks within a drape container of a thermal treatment system basin. The thermal treatment system thermally treats a sterile surgical liquid placed within the drape container and may be of the types disclosed in U.S. Pat. No. 4,393,659 (Keyes et al.), U.S. Pat. No. 4,934,152 (Templeton), U.S. Pat. No. 5,163,299 (Faries, Jr. et al.), U.S. Pat. No. 5,331,820 (Faries, Jr. et al.), U.S. Pat. No. 5,333,326 (Faries, Jr. et al.), U.S. Pat. No. 5,400,616 (Faries, Jr. et al.), U.S. Pat. No. 5,402,644 (Faries, Jr. et al.), U.S. Pat. No. 5,429,801 (Faries Jr. et al.), U.S. Pat. No. 5,457,962 (Faries, Jr. et al.), U.S. Pat. No. 5,502,980 (Faries, Jr. et al.), U.S. Pat. No. 5,522,095 (Faries, Jr. et al.), U.S. Pat. No. 5,524,643 (Faries, Jr. et al.), U.S. Pat. No. 5,551,240 (Faries, Jr. et al.), U.S. Pat. No. 5,615,423 (Faries, Jr. et al.), U.S. Pat. No. 5,653,938 (Faries, Jr. et al.), U.S. Pat. No. 5,809,788 (Faries, Jr. et al.), U.S. Pat. No. 5,816,252 (Faries, Jr. et al.), U.S. Pat. No. 5,857,467 (Faries, Jr. et al.), U.S. Pat. No. 5,862,672 (Faries, Jr. et al.), U.S. Pat. No. 5,879,621 (Faries, Jr. et al.), U.S. Pat. No. 5,950,438 (Faries, Jr. et al.), U.S. Pat. No. 6,003,328 (Faries, Jr. et al.), U.S. Pat. No. 6,035,855 (Faries, Jr. et al.), U.S. Pat. No. 6,087,636 (Faries, Jr. et al.), U.S. Pat. No. 6,091,058 (Faries, Jr. et al.), U.S. Pat. No. 6,255,627 (Faries, Jr. et al.), U.S. Pat. No. 6,371,121 (Faries, Jr. et al.), U.S. Pat. No. 6,860,271 (Faries, Jr. et al.), U.S. Pat. No. 6,918,395 (Faries, Jr. et al.) and U.S. Patent Application Publication Nos. 2004/0200483 (Faries, Jr. et al.) and 2004/0208780 (Faries, Jr. et al.). The disclosures in the above-mentioned patents and patent application publications are incorporated herein by reference in their entireties.

2. Discussion of the Related Art

The above-referenced Keyes et al. patent (U.S. Pat. No. 4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent (U.S. Pat. No. 4,934,152), the Keyes et al. system has a number of disadvantages. In particular, the separate product basin must be removed and re-sterilized after each use. Additionally, the glycol or other thermal transfer medium is highly flammable or toxic and, in any event, complicates the procedure. The Templeton patent (U.S. Pat. No. 4,934,152) discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al. patent (U.S. Pat. No. 5,163,299) notes that scraping congealed liquid from the drape is undesirable in view of the potential for damage to the drape, resulting in a compromise of sterile conditions. As a solution to the problem, the Faries, Jr. et al. patent (U.S. Pat. No. 5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel. Accordingly, several of the Faries, Jr. et al. patents (e.g., U.S. Pat. Nos. 5,331,820; 5,400,616; 5,457,962; 5,502,980; 5,653,938; 5,809,788; 5,857,467; 5,950,438; 6,003,328; and 6,035,855) resolve the problem of manual drape manipulation by disclosing various techniques and/or dislodgment mechanisms to automatically remove the congealed liquid adhering to the drape without endangering the integrity of the drape.

The Templeton patent (U.S. Pat. No. 4,934,152) further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, several of the Faries, Jr. et al. patents (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627) disclose a manner in which to simultaneously provide both surgical slush and warmed surgical liquid during a surgical procedure by utilizing a machine having plural basins with each basin either producing surgical slush or heating a sterile liquid. This machine typically utilizes a single surgical drape that forms a drape receptacle within each basin to collect sterile slush and heated sterile liquid produced by the machine in the respective basins.

In addition, several of the drapes and thermal treatment systems disclosed in the above-mentioned patents include specialized features to enhance various aspects of thermal treatment system operation. For example, some of the specialized features may include: bladder drapes (e.g., as disclosed in U.S. Pat. Nos. 5,809,788; 5,950,438; and 6,003,328); drapes having plates or disks (e.g., as disclosed in U.S. Pat. Nos. 5,457,962 and 5,502,980); reinforced drapes (e.g., as disclosed in U.S. Pat. No. 5,857,467); drape indicators and corresponding thermal treatment system detection devices to ensure sterility by enabling system operation in response to detecting a sterile drape placed on the system (e.g., as disclosed in U.S. Pat. Nos. 5,653,938 and 5,879,621); drapes having indicia to direct placement of the drapes on thermal treatment systems (e.g., as disclosed in U.S. Pat. No. 5,615,423); surgical drapes constructed of materials having a coefficient of friction in a particular range and/or drapes including attachment mechanisms such that a drape may withstand being drawn under a dislodgment mechanism (e.g., as disclosed in U.S. Pat. No. 6,035,855); a stand to elevate objects within a heated basin above the basin floor (e.g., as disclosed in U.S. Pat. No. 6,087,636) and/or a heater configured to cover a portion of the basin (e.g., as disclosed in U.S. Pat. Nos. 6,091,058 and 6,255,627) to prevent the drape from overheating and puncturing when objects are placed within the basin; and remote control of a thermal treatment system (e.g., as disclosed in U.S. Pat. Nos. 6,371,121, 6,860,271 and 6,918,395).

However, when insignificant amounts of liquid are present within a thermal treatment system basin, the system heating and cooling mechanisms operate with minimal thermal resistance, thereby enabling the mechanisms to become damaged. Further, the drapes employed by the system may be damaged by being disposed proximate the heating or cooling mechanism without having the liquid to absorb the thermal energy. Since only sterile drapes are to be used during surgical procedures, a leak in a surgical drape compromises sterility and contaminates the entire surgical procedure, thereby increasing the risk of injury to a patient.

The related art has attempted to overcome this problem by employing sensing devices with surgical drapes. For example, U.S. Pat. No. 5,524,643 (Faries, Jr. et al.) discloses a surgical drape combined with a sensor, preferably attached to the drape, to detect the presence of liquid within a drape container conforming to a heating/cooling thermal treatment system basin. An alternative embodiment employs sensors at opposite surfaces of the drape to measure conductance and, thereby, leakage through the drape. A microprocessor of each embodiment receives a signal representing, for example, an electrical conductance measurement and determines the presence of liquid and/or a leak. If liquid is not present or a leak is determined to exist, the microprocessor disables a temperature controller for the basin to prevent damage to the drape and heating and cooling mechanisms.

U.S. Pat. No. 5,816,252 (Faries, Jr. et al.) discloses a drape for use with a system for thermally treating a sterile medium. The drape includes liquid sensitive material that changes color upon contact with liquid to indicate the presence of a leak. The liquid sensitive material may be placed between the drape and a receiving basin or affixed to the drape in the form of indicia symbolically directing placement of the drape over the system. The system may include a single basin and be of the type that either thermally cools or heats the sterile medium, or the system may include a plurality of basins with each basin either thermally cooling or heating the sterile medium. The liquid sensitive material detects leaks within the drape while assisting the operator in properly aligning and placing the drape over the system.

The above-described systems can stand some improvement. In particular, the Faries, Jr. et al. sensor drape (U.S. Pat. No. 5,524,643) employs a plug connector disposed through the drape to facilitate connections between the drape sensor and the thermal treatment system, thereby complicating the process of effectively sealing the drape to prevent contamination of the sterile field. Further, the drape is required to be placed on the system with the plug aligned with a corresponding plug receptacle for system operation, thereby restricting the manners in which the drape may be positioned on the system to form the drape container. The Faries, Jr. et al. system employing liquid sensitive material with a drape (U.S. Pat. No. 5,816,252) indicates the presence of a leak within the drape container. However, this system relies on operating room personnel to respond to the leak indication and perform appropriate actions with respect to system operation. Thus, the system may continually operate in the presence of a drape container leak until personnel notice and respond to the leak indication, thereby increasing the risk of contamination of a surgical procedure and damage to the system heating or cooling mechanism when a drape leak occurs.

OBJECTS AND SUMMARY OF THE INVENTION

Accordingly, it is an object of the present invention to detect the presence of solution and/or a leak within a drape container disposed in a thermal treatment system basin and control system operation in accordance with detected drape container conditions.

It is another object of the present invention to dispose a conductor or other object through a sterile surgical drape while maintaining the sterile field.

Yet another object of the present invention is to employ a surgical drape including solution and/or leak sensors with a thermal treatment system including circuitry that interfaces the drape to control system operation in accordance with drape conditions detected by the sensors and circuitry.

still another object of the present invention is to limit utilization of a sterile surgical drape to a single use to maintain sterility of drapes for medical procedures.

A further object of the present invention is to detect tampering with a sterile surgical drape to prevent the drape from being used plural times with a thermal treatment system, thereby ensuring use of a sterile drape for medical procedures.

The aforesaid objects may be achieved individually and/or in combination, and it is not intended that the present invention be construed as requiring two or more of the objects to be combined unless expressly required by the claims attached hereto.

According to the present invention, a drape including a sensing device is disposed over a top surface of a thermal treatment system having a basin recessed therein. A portion of the drape is pushed down into, and conforms to, the basin to form a drape container or receptacle within the basin for collecting a sterile medium. The thermal treatment system may be of the type that either heats or congeals the sterile medium to respectively produce a warm sterile liquid or sterile slush within the basin. The sensing device includes electrodes that are typically disposed through the drape and sealed. The electrodes provide signals indicating the presence of liquid and/or leaks or other conditions within the drape container to the system to facilitate control of system operation. In addition, the sensing device includes a fuse to limit the drape to a single use. The system disables the fuse to indicate prior use and detects tampering to bypass the fuse, thereby preventing use of the drape for subsequent medical procedures.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
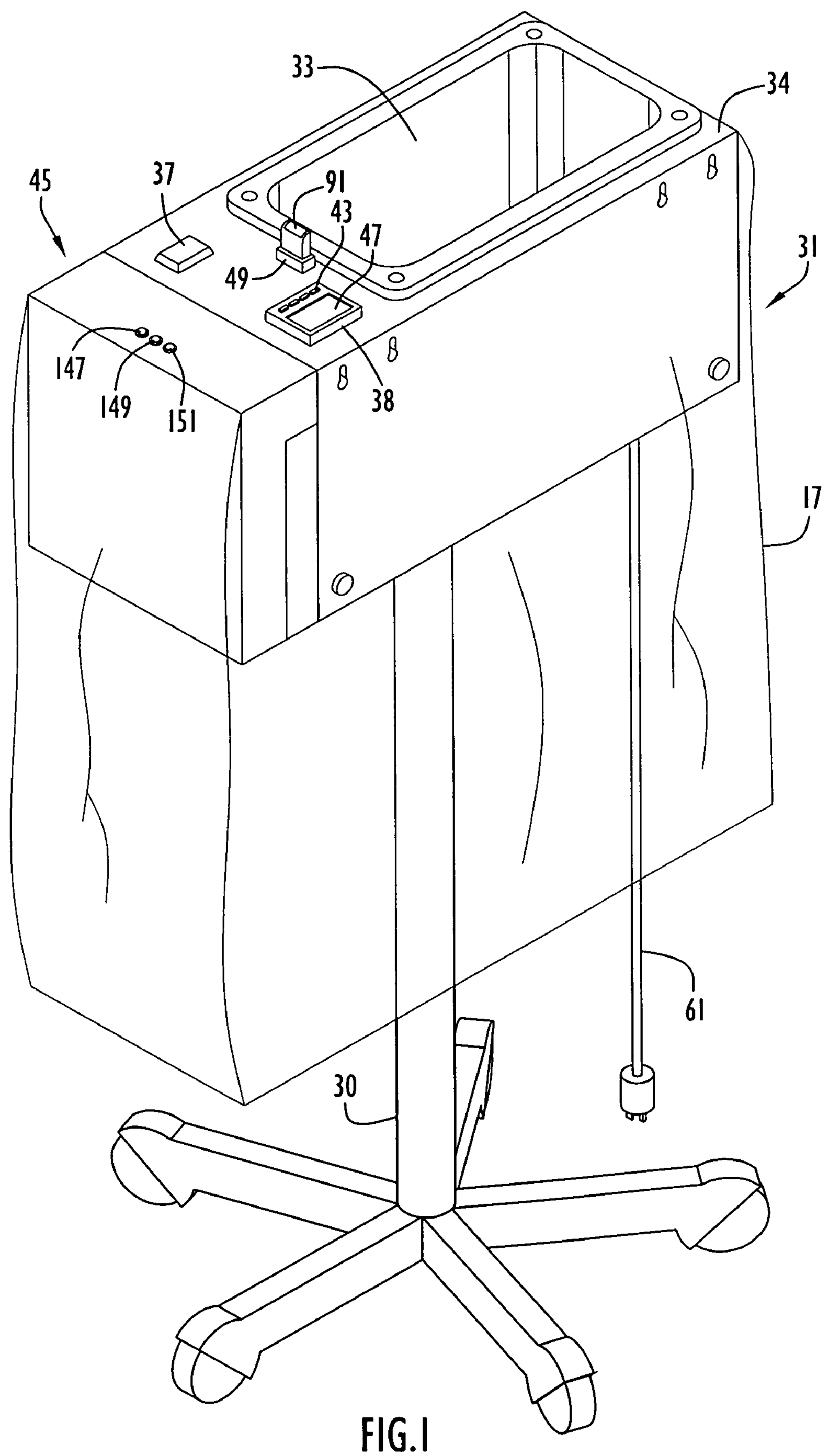
FIG. 1 is a view in perspective of a surgical drape placed over an exemplary thermal treatment system to detect fluid and leaks within a thermal treatment system basin according to the present invention.

An exemplary thermal treatment system and drape to heat a sterile medium (e.g., solution or liquid) and detect drape container conditions according to the present invention is illustrated in FIG. 1. Specifically, the system includes a cabinet or housing 31, a wiring housing 45 attached to the cabinet and a warming basin 33 recessed into a cabinet top surface 34. The cabinet or housing may be disposed on a stand 30, preferably including casters or rollers for transport, or be utilized on a table or counter top. Basin 33 may be of any shape; however, by way of example only, the basin is illustrated as being substantially rectangular. A power switch 37 and a temperature controller/indicator 38 are provided on top surface 34 adjacent basin 33 and toward wiring housing 45. The wiring housing is attached to the cabinet side wall that is closest to power switch 37 and facilitates connections as described below. A receptacle 49 is disposed on top surface 34 between the power switch and temperature controller to couple a drape to the system as described below. A heater 70 (FIG. 9) is disposed on the underside and/or sides of the basin to heat the basin and the sterile medium contained therein. The heater is controlled by controller 38 in accordance with an entered desired temperature and temperatures measured by a temperature sensor 72 (FIG. 9) as described below. Heater 70 is typically implemented by a conventional etched foil silicon rubber heating pad and is attached to the basin via a pressure sensitive or other type of adhesive. The heater may alternatively be of any quantity (e.g., at least one), shape or size, and may include any configuration (e.g., strips, bars, segments, etc.) that covers the entirety or any portion of the basin. In addition, the heater may be implemented by any conventional or other type of heater or heating element (e.g., heating coils, etc.) that may be disposed on the basin at any suitable locations.

Temperature sensor 72 is preferably implemented by a conventional resistive temperature device (RTD) (e.g., a 1,000 Ohm RTD). However, the sensor may be implemented by any conventional or other type of temperature sensor, and may be disposed at any suitable location on the basin or within the cabinet. It is to be understood that the thermal treatment system described above may have various configurations. For example, the thermal treatment system may be configured to cool and/or congeal the medium to produce cooled liquid or surgical slush. In this instance, the heater may be replaced by refrigeration devices that are controlled in substantially the same manner described below in response to detection of solution and leaks within the drape container. Further, the thermal treatment system may include a plurality of basins warming and/or cooling a sterile medium. Examples of warming, cooling and/or plural basin systems are disclosed in several of the above-mentioned Faries, Jr. et al. patents (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627).

A sterile drape 17, preferably transparent, is typically disposed over the top and sides of cabinet 31 and made to conform to the side wall and bottom of basin 33. Power switch 37 and controller 38 are disposed on top surface 34 of system cabinet 31 and are adjustable manually through drape 17. The portion of drape 17 disposed in basin 33 serves as a sterile container or receptacle for sterile liquid placed therein to be heated. Typical sterile liquid treated by the thermal treatment system is a 0.80% to 0.95% sodium chloride solution (i.e., saline). Drape 17 is made from materials that are impervious to the sterile liquid and sufficiently soft and flexible to conform to a basin wall. The thickness of the drape is preferably minimized to render thermal transfer therethrough most efficient, yet the thickness is sufficient to resist tearing and puncturing during normal use. The drape may be made of materials commonly used in hospitals for surgical drapes, or may be made of polyurethane film as disclosed for the drape in U.S. Pat. No. 4,934,152 (Templeton). The drape typically includes a conductivity above 100,000 Ohms in order to enable a sensing device to detect drape conditions as described below. Alternatively, the drape may be non-conductive and use sensors to detect drape conditions as described below.

The drape may further include a preformed container portion contoured to match the contour of a basin. The preformed container portion may be (but is not necessarily) thicker than the remaining portions of the drape described above in order to resist puncture and enable the container portion to maintain the shape of the basin. By way of example only, the container portion may be made of a heavy gauge polyethylene/ionomer resin blend. The percentage of ionomer resin in the blend is typically (but not necessarily) in the approximate range of forty to seventy percent. The drape is designed to be disposable after a single use to enhance patient safety and is provided presterilized and prepackaged in a manner to preserve its sterile state during storage.

The drape is typically positioned over the thermal treatment system with a portion of the drape disposed in a basin to form a drape receptacle as described above. The drape forms a sterile field above the basin to maintain sterility of the sterile medium. However, a puncture, tear or other opening in the drape disrupts the sterile field and may contaminate the sterile liquid, thereby risking injury to a patient. Further, the thermal treatment system may damage the drape (e.g., via the heating or refrigeration device) in the event that liquid is not present within the drape container.

Figure 2:
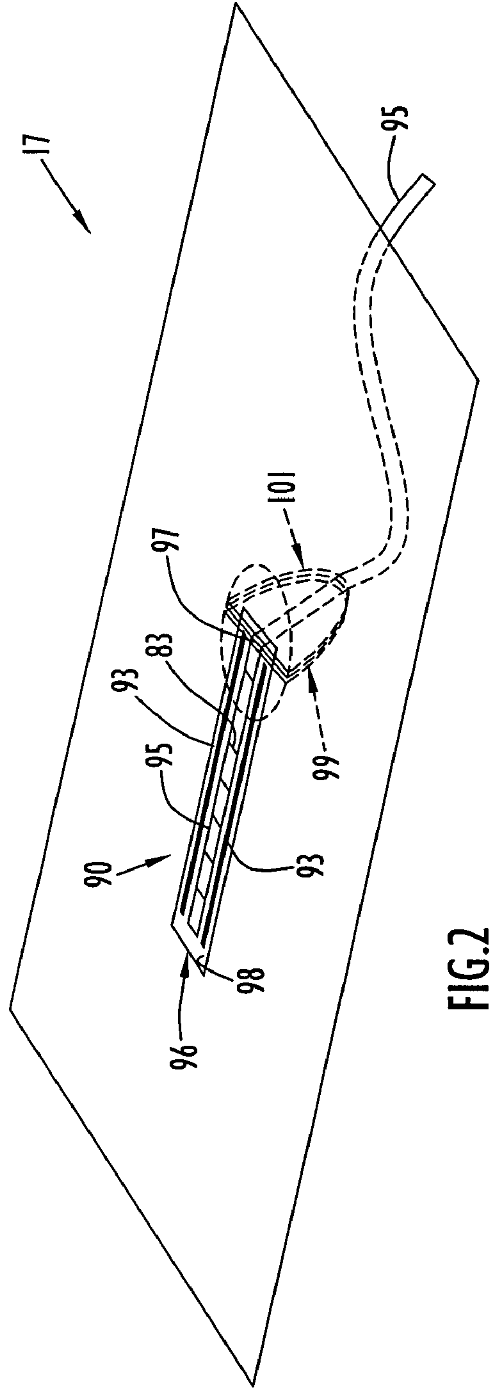
FIG. 2 is a view in perspective of the surgical drape of the present invention for detecting the presence of fluid and leaks within a thermal treatment system basin.
Figure 3:
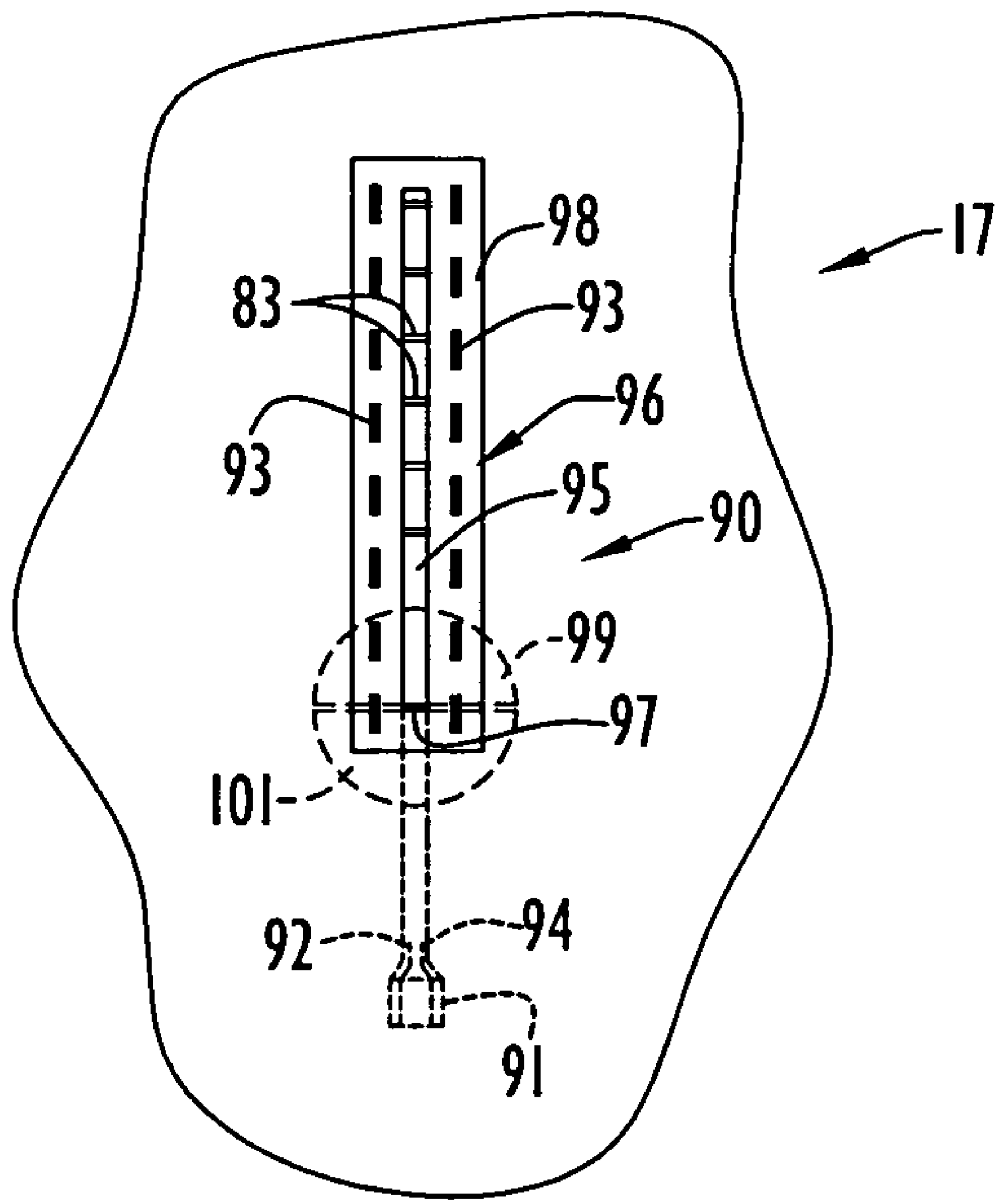
FIG. 3 is a top view in plan of the sensing device of the drape of FIG. 2.

In order to detect the presence of liquid and/or leaks within the drape container to maintain drape integrity and sterility of the sterile medium, drape 17 includes a sensing device as illustrated in FIGS. 2-3. Specifically, drape 17 is substantially rectangular and includes a sensing device 90 to detect the presence of liquid and leaks within a drape container. Sensing device 90 includes a pair of electrodes 92, 94 that are affixed to a generally rectangular strip 95 disposed on an intermediate portion of the drape sterile surface. The electrodes are disposed on the electrode strip and extend substantially in parallel. Electrode strip 95 may further include electrodes 292, 294 with a sensor 272 disposed therebetween (FIG. 6) to measure various conditions (e.g., temperature, withdrawal of liquid from the basin, etc.) within the basin as described below. The electrodes of strip 95 are preferably implemented by traces of silver or other metallic ink, but may be implemented by any suitable conductors (e.g., wires, strips, etc.). The electrode strip is enclosed, in whole or in part, within a pouch 96 to secure the electrodes to the drape and to protect the electrodes from sharp objects that may be disposed within the basin. In addition, the pouch assists to prevent grounding of electrodes 92, 94 or formation of a current flow path therebetween due to placement of conductive objects (e.g., instruments, stainless steel pitchers, etc.) in the basin that may produce erroneous detections. The pouch is preferably formed from a substantially rectangular segment or flap 98 that is attached via any conventional or other techniques (e.g., heat welding, RF, heat sealing, press or UV curing, pressure, etc.) to the drape sterile surface and sealed by seams 93, each formed toward and extending along a respective flap longer dimensioned edge. The seams may be continuous (FIG. 2) or intermittent (FIG. 3) to allow greater circulation of liquid over, around and/or through pouch 96 to better facilitate the heating and/or cooling of liquid. The pouch may be of one uniform surface or wedges that may include holes, slits, lattices, cross-hatches or other manners of access for the liquid to allow greater circulation.

The distal ends of the electrodes are attached to a plug or connector 91 that interfaces detection circuitry within the thermal treatment system as described below. The plug includes electrode traces disposed on a plug rear surface. The distal portions of strip 95 (and the electrodes) pass through the drape from the sterile to the non-sterile drape sides via an opening or slit 97 defined in the drape at an intermediate location. Substantially circular segments or patches 99, 101 are attached to the non-sterile drape surface and to each other to seal opening 97 and strip 95. The patches are each basically in a folded configuration to encompass and seal the opening and strip in order to prevent escape of liquid from, and maintain sterility of, the drape container as described below.

Figure 4:
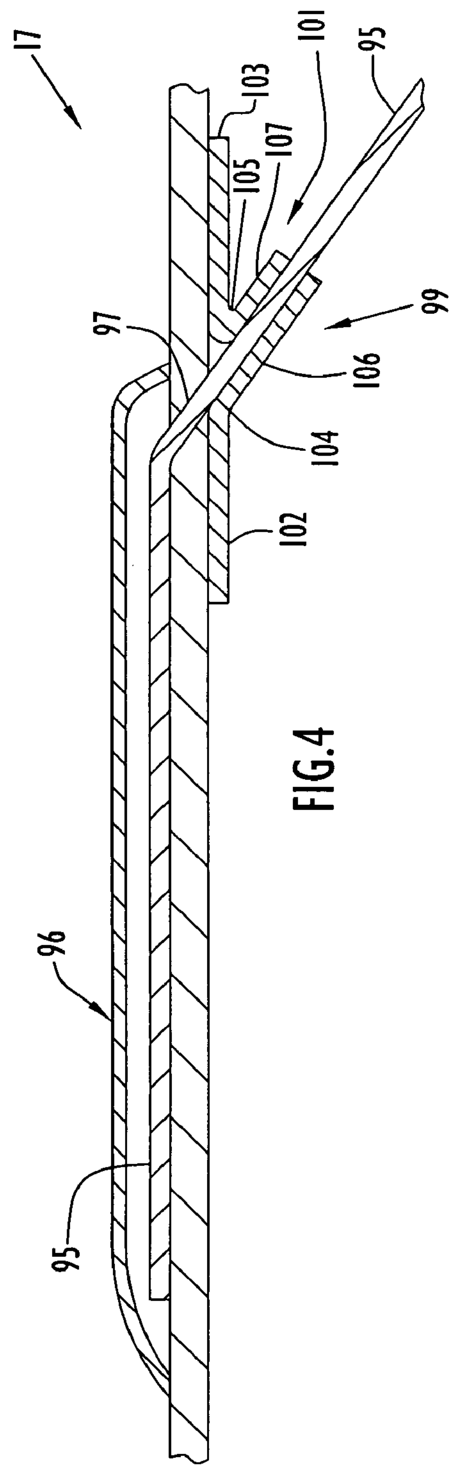
FIG. 4 is a side view in elevation and section of the surgical drape of FIG. 2.

Referring to FIG. 4, patches 99, 101 are each attached to the drape non-sterile surface on respective opposing sides of opening 97. Patch 99 includes a drape engagement section 102, a fold or bend 104 disposed at an intermediate patch location and a transverse section 106 extending transversely relative to drape 17 from fold 104. Drape engagement section 102 of patch 99 is attached to the non-sterile drape surface coincident pouch 96 with fold 104 disposed proximate opening 97. Patch 99 may be attached to the drape via any conventional or other techniques (e.g., heat welding, RF, heat sealing, press or UV curing, adhesives, pressure, etc.). Transverse section 106 extends in a transverse direction relative to the drape from fold 104 and along the bottom surface of strip 95 extending through opening 97.

Patch 101 is substantially similar to patch 99 and includes a drape engagement section 103, a fold or bend 105 disposed at an intermediate patch location and a transverse section 107 extending transversely relative to drape 17 from fold 105. Drape engagement section 103 of patch 101 is attached to the drape non-sterile surface on the side of opening 97 opposing patch 99. Patch 101 may be attached to the drape via any conventional or other techniques (e.g., heat welding, RF, heat sealing, press or UV curing, adhesives, pressure, etc.). Fold 105 is disposed proximate opening 97 with transverse section 107 extending in a direction transverse to the drape from the fold along the top surface of strip 95. The electrode strip is basically disposed between the transverse sections of patches 99, 101, where the transverse patch sections are fused or attached to each other and/or the drape non-sterile surface via any conventional or other techniques (e.g., heat welding, RF, heat sealing, press or UV curing, adhesives, pressure, etc.) to effectively seal opening 97 and a portion of strip 95. The strip extends beyond the sealed patches for connection to the detection circuitry as described below. Flap 98 and patches 99, 101 are preferably constructed of drape materials; however, the flap and patches may be constructed of any suitable materials, may be of any shape or size, and may be disposed on the drape at any suitable locations via any conventional or other techniques.

Referring back to FIGS. 1-3, sensing device 90 detects the presence of liquid and leaks within the drape container in response to placement of drape 17 over the thermal treatment system. In particular, current flow between electrodes 92, 94 is initiated in response to these electrodes contacting liquid. The liquid (or current flow) causes a respective change in resistance (or voltage) along a circuit path within detection circuitry of the thermal treatment system that includes electrodes 92, 94. The changes indicate drape container conditions and are detected by the detection circuitry as described below. In order to enable the liquid in the drape container to contact electrodes 92, 94 and facilitate the above changes in the circuit path characteristics, flap 98 includes a series of slots or other openings (e.g., holes, slits, cross-hatches, lattices, etc.) 83. The slots or openings are defined in the flap between seams 93 and are spaced from each other in a direction of the flap longer dimension. If the slots are utilized, they are generally rectangular and extend substantially perpendicular to electrodes 92, 94. Each slot includes a longer dimension substantially similar to the width of strip 95 and encompasses portions of each electrode 92, 94 to facilitate enhanced exposure of the electrodes to liquid within the drape container. Alternatively, flap 98 may include a series of openings (not shown) defined therein to permit contact between the liquid and electrodes. Flap 98 may include any quantity of slots and/or openings of any shape or size and disposed at any locations in any desired fashion to facilitate contact between the electrodes and liquid within the drape container.

Current flow between electrodes 92, 94 is initiated in response to those electrodes contacting liquid, where the liquid (or current flow) causes a respective change in resistance (or voltage) along the circuit path within the detection circuitry as described above that indicates the presence of solution within the drape container. Further, the presence of a leak within the drape container enables current to flow between electrodes 92, 94 and ground (e.g., the basin beneath the drape), thereby providing a further change in resistance (or voltage) along that circuit path. The detection circuitry within the thermal treatment system detects the changes to determine drape container conditions. In particular, the detection circuitry initially applies a reference voltage or potential to electrodes 92 and/or 94. This potential may be provided in an intermittent fashion to prevent solution within the basin from attaining a charge which may affect the current flow between electrodes 92, 94 and cause erroneous detections. Since electrodes 92, 94 are electrically isolated from each other within strip 95 as described above, current flow between the electrodes is prevented and the potential of and between those electrodes basically remains unchanged.

When the sterile medium is placed in the drape container, the sterile medium contacts electrodes 92, 94, thereby forming an electrical path or conductive bridge between those electrodes. Accordingly, current flow between electrodes 92, 94 is initiated in response to those electrodes contacting liquid, thereby causing a change in the resistance (or voltage) along a circuit path within the detection circuitry including electrodes 92, 94 as described above. Further, the presence of a leak within the drape container enables current to flow between electrodes 92, 94 and ground (e.g., the basin beneath the drape), thereby causing a further change in the resistance (or voltage) along that circuit path. The changes to the circuit path characteristics resulting from each of the above conditions is detected by the detection circuitry within the thermal treatment system. This is typically accomplished by detecting the voltage (or resistance) along the circuit path including electrodes 92, 94. The resistance (or voltage) change in the circuit path due to the presence of liquid or a leak is utilized by the detection circuitry to detect the presence of solution and/or leaks within the drape container and to control system operation in accordance with the detected conditions as described below. For example, the detection circuitry may disable the thermal treatment system in response to the absence of liquid or the presence of a leak within the drape container. In addition, the detection circuitry may receive signals from electrodes 292, 294 to determine the conditions sensed by sensor 272 (e.g., temperature, withdrawal of solution, etc.).

Wiring housing 45 (FIG. 1) receives signals from the electrode strip via receptacle 49, and includes wiring to transfer signals between that housing and detection circuitry 100 (FIG. 9) to facilitate detection of liquid and/or leaks and other conditions within the drape container. Wiring housing 45 is in the form of a generally rectangular box and is mounted on a cabinet side wall. The wiring housing includes indicators, preferably in the form of light emitting diodes 147, 149 and 151 to indicate drape container conditions. By way of example only, the wiring housing includes: green diode 147 to indicate operation of the system (e.g., solution present without a drape container leak); yellow diode 149 to indicate the absence of solution and leaks within the drape container; and red diode 151 to indicate the presence of a leak within the drape container. The wiring housing may alternatively be disposed at any location on cabinet 31 (e.g., top surface, side walls, cabinet interior, etc.), while the receptacle may be disposed at any location on the cabinet or wiring housing.

Figure 5:
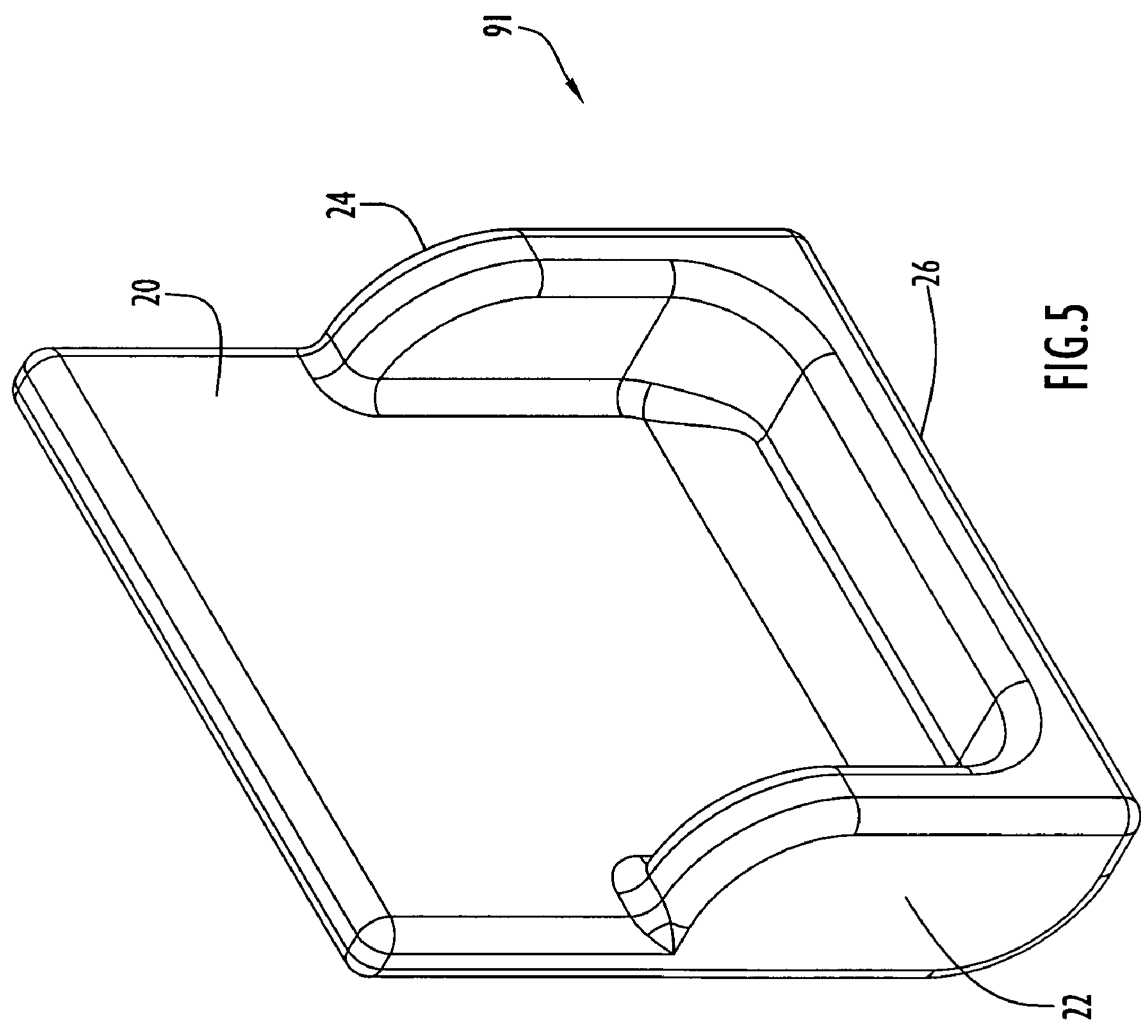
FIG. 5 is a perspective view of a plug of the drape sensing device of FIG. 2 for engaging the thermal treatment system.
Figure 6:
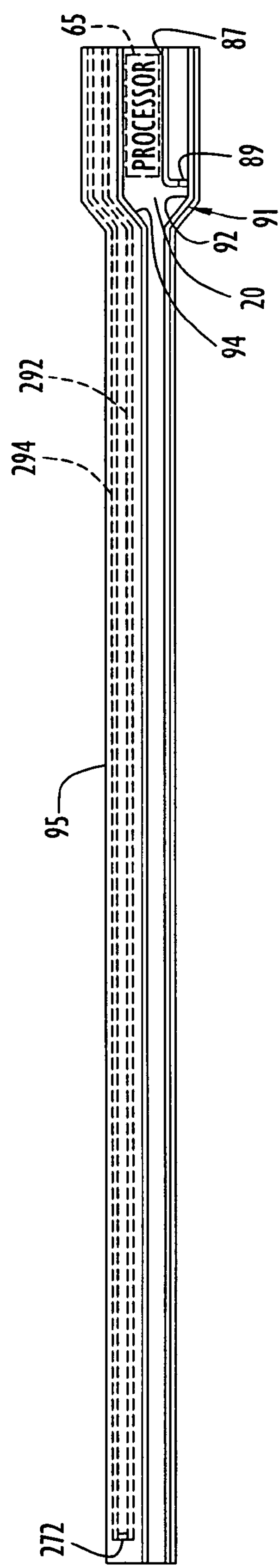
FIG. 6 is a view in elevation of the electrodes and plug of the drape sensing device of FIG. 2.

Plug or connector 91 is illustrated is FIGS. 5-6. Specifically, plug 91 includes a rear panel 20 with a substantially 'U'-shaped projection 25 attached to the lower portion of the front surface of the rear panel. The plug includes an open front portion with the projection defined by side walls 22, 24 and a bottom wall 26. Electrodes 92, 94 extend from strip 95 and are disposed on the back surface of rear panel 20. Further, an electrode 87 is disposed on the panel back surface and coupled to electrode 92 via a fuse 89. Electrode 87 provides signals to enable determination of the status of the fuse (e.g., enabled or disabled) by the thermal treatment system. The fuse status is utilized to indicate prior use of the drape to the thermal treatment system to control system operation as described below.

In addition, electrode strip 95 may further include electrodes 292, 294 with sensor 272 disposed therebetween (FIG. 6) to measure various conditions (e.g., temperature, withdrawal of liquid from the basin, etc.) within the basin. Electrodes 292, 294 extend from strip 95 and are preferably covered with a non-conductive coating and disposed on the back surface of rear panel 20 to provide signals from sensor 272 for processing. The electrode strip may include any quantity of electrodes and sensor arrangements to measure various conditions. For example, the electrode strip may include a sensor 272 in the form of a temperature or humidity sensor (e.g., surface mounted diode, integrated circuit (IC) or semiconductor temperature sensor, temperature diode, etc.), where electrodes 292, 294 provide signals indicating solution temperature or other conditions to control circuitry within cabinet 31 for control and/or documentation purposes.

Alternatively, the electrode strip may include a sensor 272 in the form of a proximity sensor to detect pitchers or other instruments in the basin, or a chemical sensor to determine placement of the correct fluid in the basin. Electrodes 292, 294 provide appropriate signals to control circuitry within cabinet 31 to process the sensor signals.

Plug 91 may alternatively include a processor 65 to enable system operation with the drape. The processor is preferably in the form of a suitably sized integrated circuit or chip and may be implemented by any conventional or other processor or processing system (e.g., microprocessor, controller, circuitry, etc.) to generate signals for the thermal treatment system. For example, the processor may be coupled to electrodes 92, 94, 292, 294 to process the electrode signals and determine drape container and fuse conditions. The processor subsequently transmits appropriate control signals to the thermal treatment system to control operation (e.g., enable the heater and/or temperature controller in response to the presence of solution, disable the heater and/or temperature controller in response to a disabled fuse, the absence of solution or the presence of a leak, control actuation of visual and/or audio indicators, etc.). The processor may provide the appropriate signals (e.g., associated with the electrodes and fuse) to receptacle 49 to enable the detection circuitry to control the thermal treatment system in the manner described below. The processor may alternatively provide signals to receptacle 49 that are transmitted to the appropriate components (e.g., heater, temperature controller, visual or audio indicators, etc.) to control system operation. In addition, the processor may be utilized in place of the fuse and store information relating to use of the drape. If the drape has prior use, the processor provides a signal indicating this status to the thermal treatment system to disable system operation.

Figure 7:
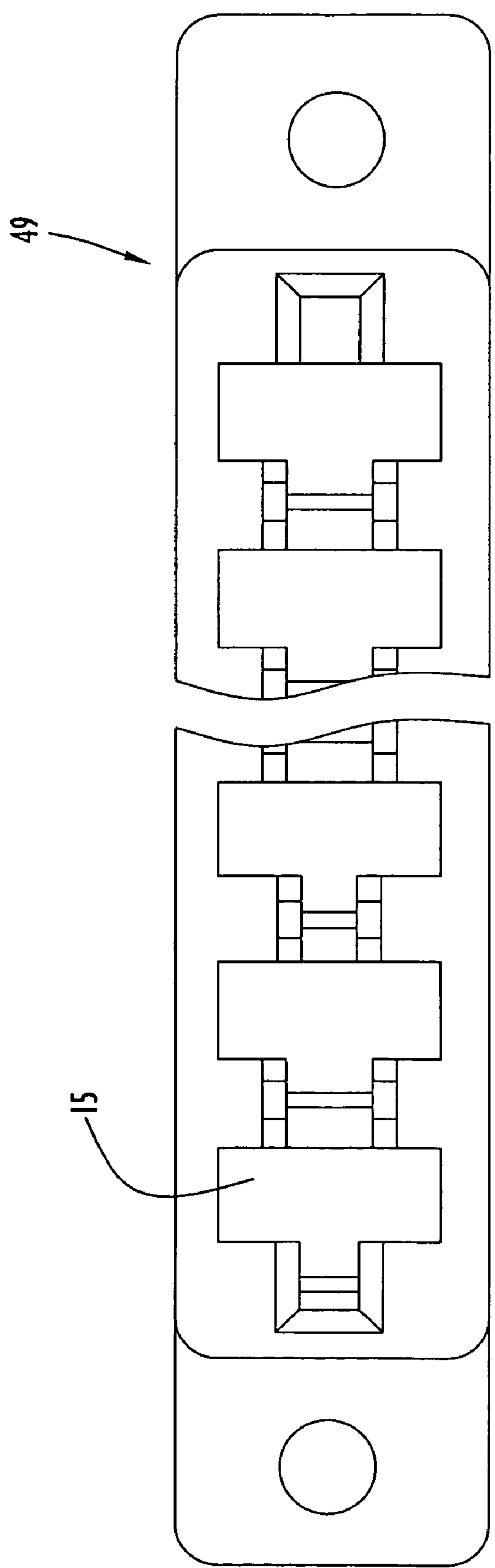
FIG. 7 is a view in plan of a receptacle of the system of FIG. 1 for receiving the plug of the drape sensing device.
Figure 8:
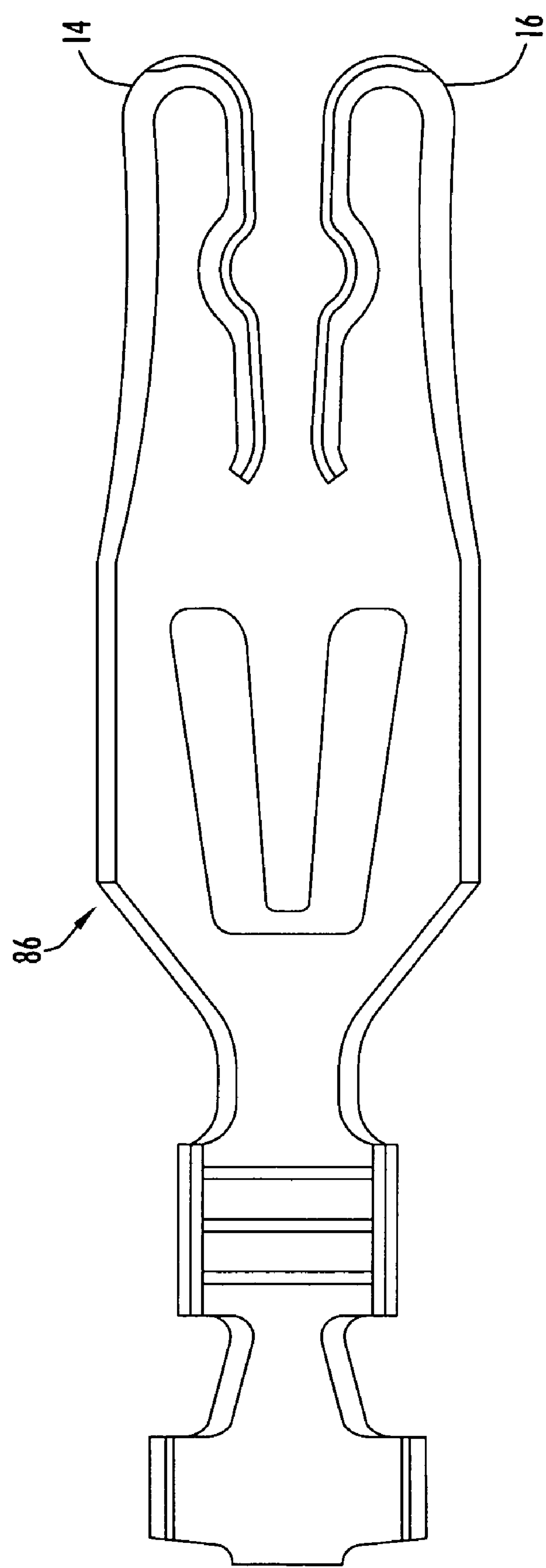
FIG. 8 is a view in elevation and partial section of contacts within the receptacle of FIG. 7 to engage electrode traces of the plug of the drape sensing device.

Receptacle 49 receives plug 91 to provide electrode signals to the thermal treatment system. Referring to FIGS. 1, 7-8, receptacle 49 includes a rectangular housing with an open top portion to receive plug 91. The open top portion is partitioned into a series of contact receptacles 15 providing contacts for the electrodes disposed on the plug. By way of example, the receptacle includes five contact receptacles 15 with three contact receptacles receiving the electrode signals (e.g., electrodes 87, 92 and 94) from the plug. However, any quantity of contact receptacles may be employed (e.g., for electrodes 292, 294) to process signals from any quantity of sensor arrangements. The contact receptacles are configured for high current to extend the life of receptacles 15 and enable repeated usage of drapes with the thermal treatment system. Each contact receptacle 15 includes a contact 86 (FIG. 8) to receive a corresponding electrode. Contact 86 is in the form of a clamp with arms 14, 16 separated by a slight distance to receive an electrode therebetween. The configuration of plug 91 enables insertion of the plug into contacts 86 of receptacles 15, where electrodes from the plug (e.g., electrodes 87, 92, 94, 292, 294) reside between arms 14, 16 of corresponding contacts 86. The 'U'-shaped projection of plug 91 serves as a stop against the distal ends of arms 16 of contacts 86. Each contact is spring biased to enable the contact arms to engage a corresponding electrode and transfer signals between that electrode and the thermal treatment system.

The system detection circuitry receives signals from the electrodes, via plug 91 and receptacle 49, and basically prevents system operation (e.g., disables controller 38) in response to a leak or the absence of liquid within the drape container, in response to the absence of a connection between the drape and the thermal treatment system, or in response to a disabled fuse indicating drape prior use. In other words, the detection circuitry determines the drape container or other conditions (e.g., from sensor 272) based on the electrode signals and controls system operation accordingly. In addition, the detection circuitry may selectively illuminate the diodes to indicate the particular determined drape container conditions (e.g., no fluid, the presence of a leak, etc.). The wiring housing receives signals from connector 91 via receptacle 49. The wiring housing further facilitates connections via appropriate wiring between the receptacle, diodes and a circuit board 52 (FIG. 9) of the detection circuitry containing a condition circuit 53 (FIG. 10) as described below. Fuses may be employed to protect the system circuitry from power surges and/or spikes that may cause damage to the system.

Figure 9:
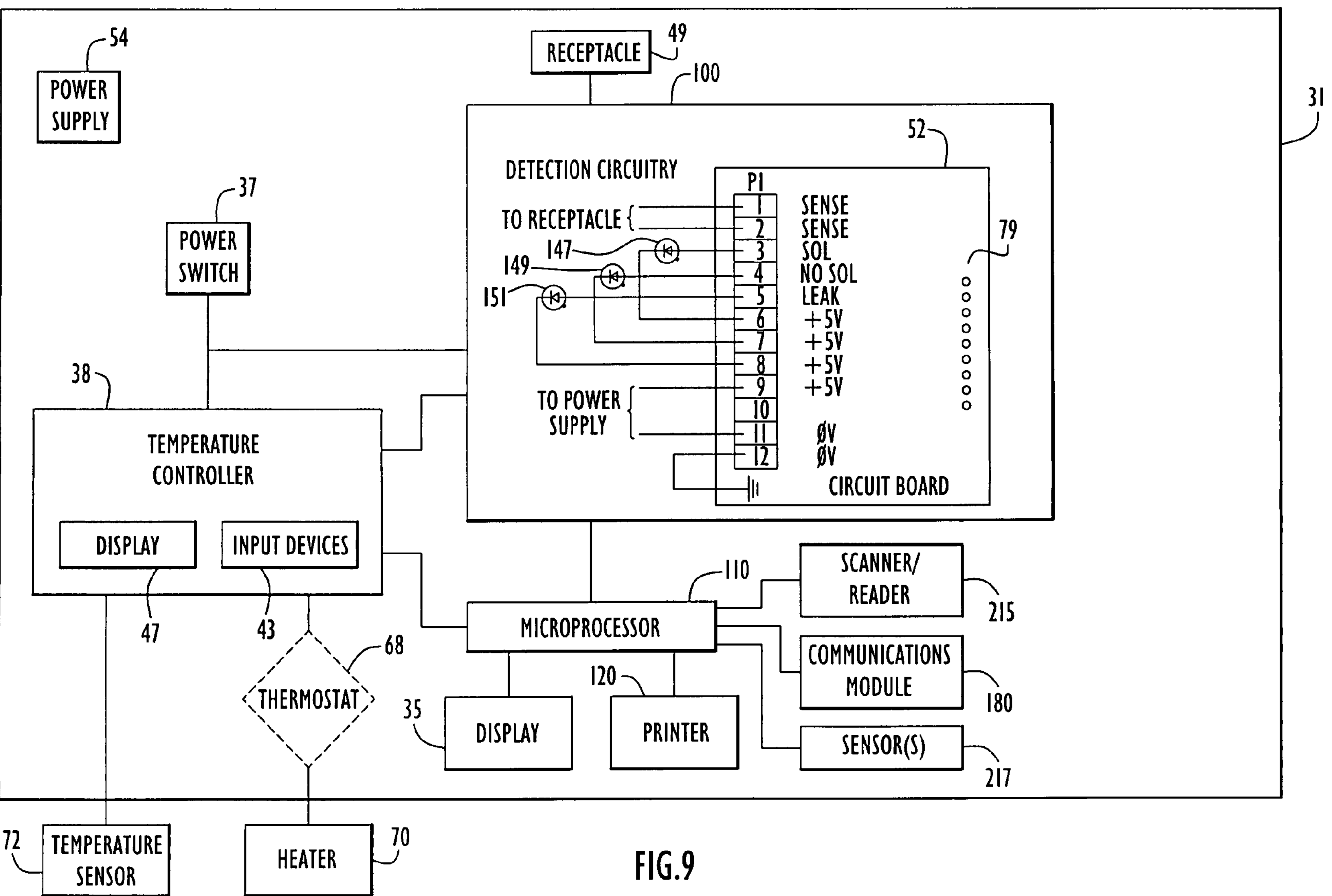
FIG. 9 is block diagram of control circuitry for the system of FIG. 1.

Referring to FIGS. 1 and 9, cabinet 31 houses control circuitry including power switch 37, temperature controller 38, receptacle 49, a power supply 54 and detection circuitry 100. Power supply 54 provides appropriate power signals to the control circuitry components and includes a receptacle to receive signals from a power cord 61 (FIG. 1) interfacing a conventional wall outlet jack. The power switch enables power to the circuitry components and may be implemented by any conventional or other switching device. Plug or connector 91 is received in receptacle 49 to transfer signals between the electrodes and the detection circuitry. This further enables the detection circuitry to detect the presence of a drape on the system as described above. The temperature controller controls the heater, while the detection circuitry determines the drape container conditions based on the electrode signals and controls the temperature controller accordingly. The wiring housing may include audio and/or visual indicators (e.g., beeper or buzzer, speaker 197 (FIG. 10), various colored light emitting diodes (e.g., green diode 147, yellow diode 149 and red diode 151), etc.) to indicate drape container conditions as described above. The detection circuitry may selectively actuate the indicators in any fashion to indicate the particular determined drape container conditions (e.g., absence of the drape or solution, the presence of a leak, etc.). The control circuitry components may be disposed on and/or within the cabinet and/or wiring housing in any fashion at any desired locations.

Temperature controller 38 is connected to heater 70 and temperature sensor 72 to control the heater in response to a desired or set point temperature entered by a user and the temperature measured by the temperature sensor. In particular, temperature controller 38 is typically implemented by a conventional temperature controller or microprocessor and includes a display 47 and input devices 43 (e.g., buttons, keys, etc.). The temperature controller controls power to the heater based on a comparison of the temperature measured by temperature sensor 72 and the set point temperature entered by the user via input devices 43. The temperature controller may further display the measured and/or set point temperatures or any other desired information on display 47. The information to display may be selected by a user via input devices 43. When the measured temperature exceeds the set point temperature, controller 38 disables or reduces power to the heater. Conversely, when the measured temperature is below the set point temperature, controller 38 enables or increases power to the heater. Alternatively, the temperature controller may control the heater in accordance with solution temperature measured by sensor 272 of electrode strip 95.

A thermostat 68 may be disposed between the controller and heater to disable current to heater 70 in response to a temperature measurement exceeding a temperature threshold. The thermostat disables the heater in response to detection of excessive heater temperatures and may be implemented by any conventional switching type or limiting devices, such as a high limit thermostat, and disposed at any suitable location.

Temperature controller 38 further controls heater 70 in response to signals received from detection circuitry 100. The detection circuitry detects the presence of solution and leaks within the drape container and provides appropriate signals to temperature controller 38. The detection circuitry basically disables the temperature controller (and heater) in response to absence of the drape, absence of solution within the drape container, a previously used or non-sterile drape, and/or the presence of a drape container leak as indicated by the electrode signals. The detection circuitry preferably includes a microprocessor to process electrode signals and control the indicators, heater or any other devices as described below.

Exemplary detection circuitry for the system includes circuit board 52 including condition circuit 53 (FIG. 10) and green, yellow and red diodes 147, 149, 151 indicating the drape container conditions. The circuit board further includes a series of pins or terminals 1-12 to facilitate connections and a plurality of indicator lights 79. By way of example only, pins 1 and 2 are connected to receptacle or connector 49 to receive signals from electrodes 92, 94, while pins 9 and 11 are connected to the positive and reference terminals of power supply 54, respectively. Pins 6-8 are connected to pin 9 and provide a voltage (e.g., +5V DC) to the condition circuit, while pin 12 is connected to pin 11 and provides a ground. Green diode 147 is connected between pins 3 and 6 and is illuminated in response to detection of solution within the drape container without a leak, while yellow diode 149 is connected between pins 4 and 7 and is illuminated in response to detection of the absence of solution and a leak within the drape container. Red diode 151 is connected between pins 5 and 8 and is illuminated in response to detection of a leak within the drape container. Pin 10 is basically inoperable and utilized to facilitate compatible connections with the board. The circuit board may include any quantity of pins to accommodate any desired inputs (e.g., electrodes 292, 294, etc.).

Figure 10:
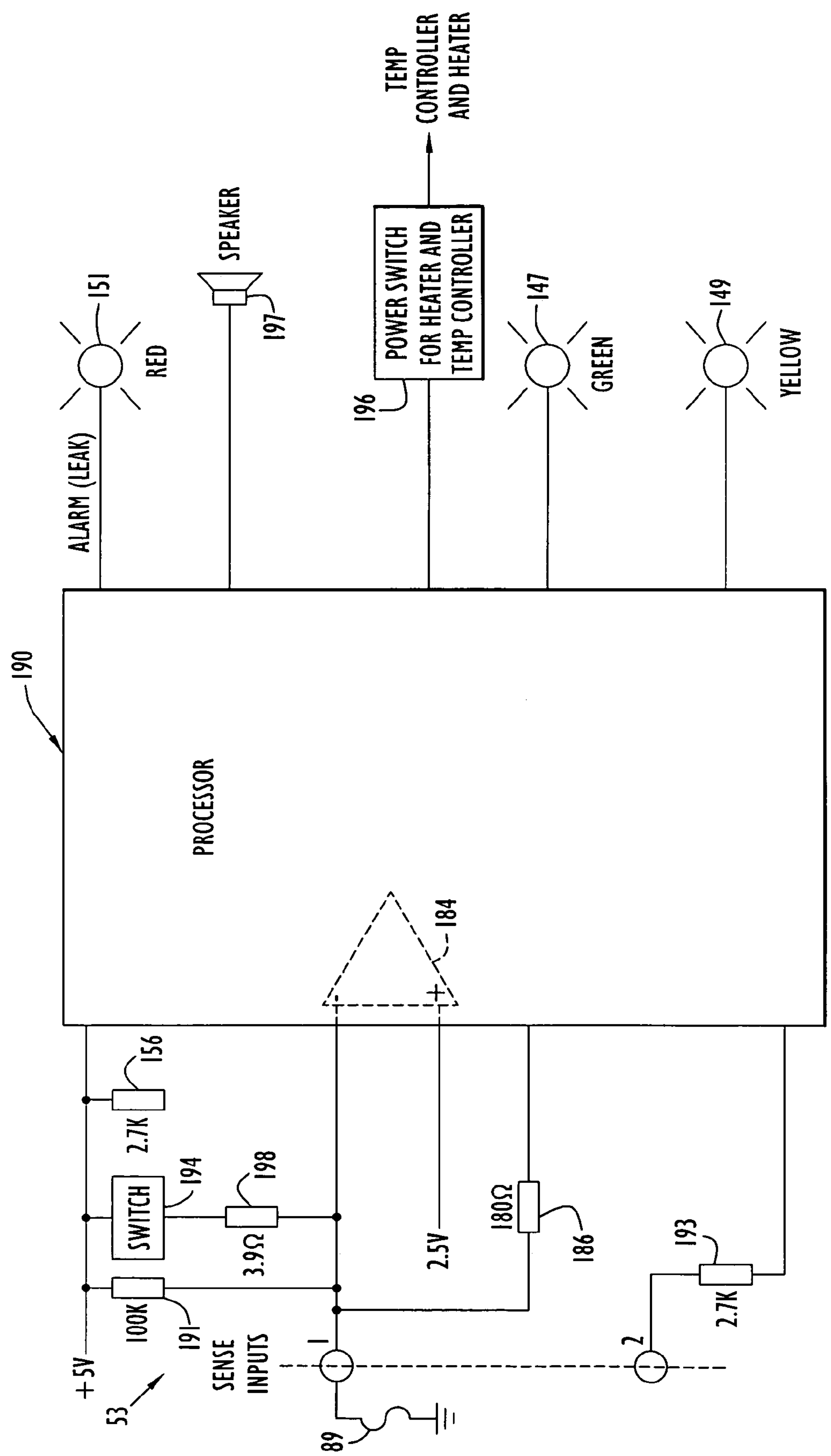
FIG. 10 is a schematic block diagram of an exemplary condition circuit of the detection circuitry within the control circuitry of FIG. 9 for determining the presence of liquid and/or leaks within a drape container.
Figure 11:
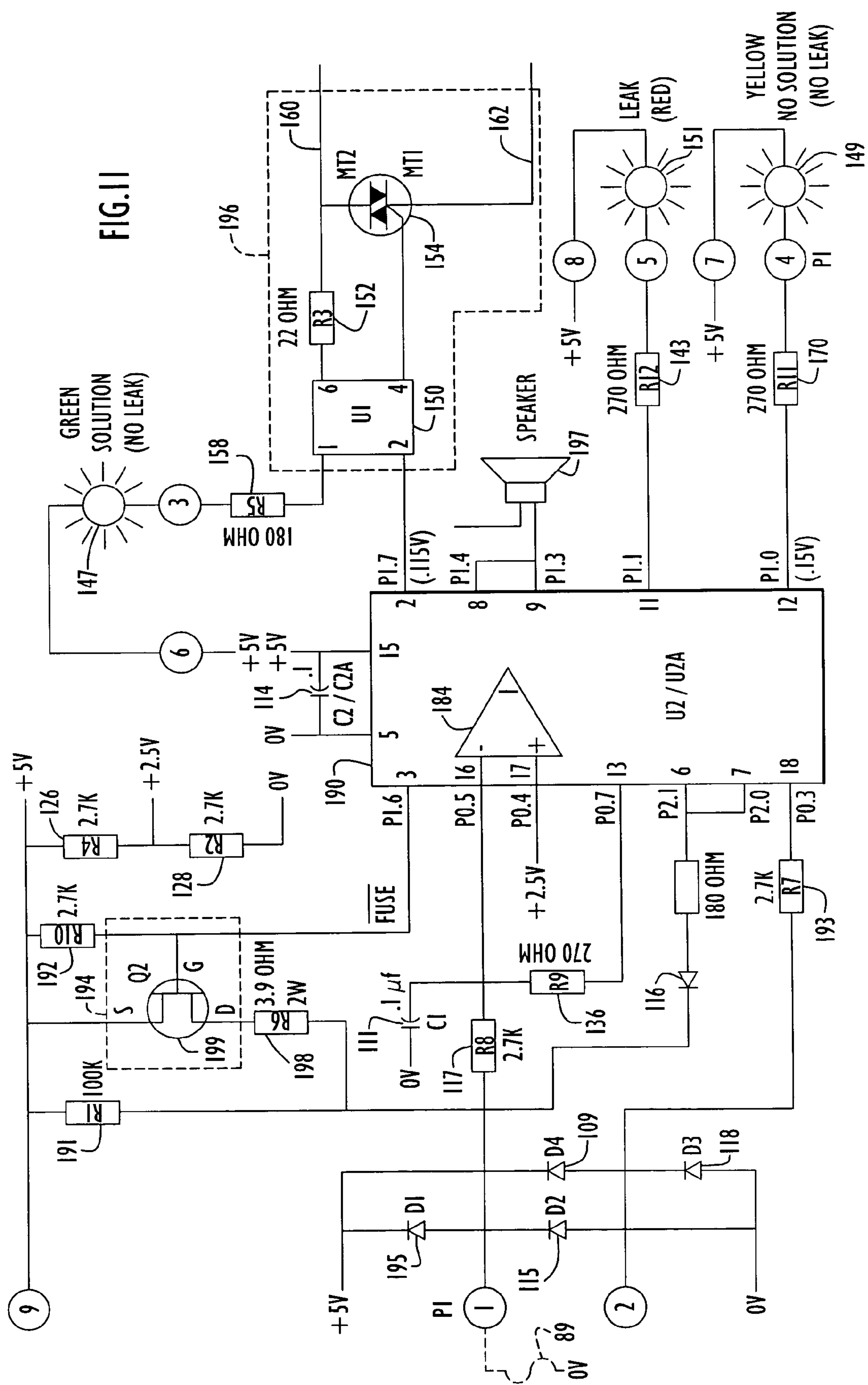
FIG. 11 is a detailed electrical schematic diagram of the exemplary condition circuit of FIG. 10.

An exemplary condition circuit 53 for detecting the presence of solution and leaks within the drape container is illustrated in FIGS. 10-11. Initially, the condition circuit prevents operation of the thermal treatment system in the event a drape is damaged (e.g., contains a leak) or not connected to the detection circuitry, in the event the fuse of plug 91 is disabled indicating prior use of the drape, or in the event solution is absent from the drape container. The condition circuit is coupled to drape electrodes 92, 94 via respective pins 1 and 2 of circuit board 52. The presence of solution within the drape container causes current flow between electrodes 92, 94 and along a circuit path within the condition circuit including those electrodes, while a leak facilitates current flow between electrodes 92, 94 and ground (e.g., the basin) as described above. Accordingly, the current flow causes a change in resistance (or voltage) in the circuit path, including pins 1 and 2 of the circuit board, thereby enabling detection of solution and leaks by the condition circuit. In particular, the condition circuit includes a microprocessor 190 (e.g., receiving supply voltage (e.g., 5V DC) and a ground with a capacitor 114 disposed therebetween) and a power switch 196. The microprocessor includes comparator logic 184 to compare signals provided to the microprocessor as described below. Pin 1 of circuit board 52 effectively provides electrode signals to an inverting input of comparator logic 184 and is coupled to fuse 89 of plug 91 via electrode 92. The inverting input is further connected to a resistor 191 (e.g., 100K Ohms) disposed in series with a supply voltage (e.g., 5V DC) and to a resistor 198 (e.g., 3.9 Ohms) connected in series with a switch 194 and the supply voltage (e.g., 5V DC). A resistor 186 (e.g., 180 Ohms) is connected between the inverting input and an output of microprocessor 190. The switch enables the system to disable fuse 89 to indicate prior use and is preferably implemented by a transistor 199 (e.g., FET, etc.) with a source coupled to the supply voltage and a drain coupled to resistor 198. The gate of the transistor is coupled to an output of microprocessor 190 and to a resistor 192 (e.g., 2.7K Ohm) disposed between the gate and the supply voltage. The switch and corresponding circuitry enable the microprocessor to disable fuse 89, while resistor 186 and the microprocessor enable detection of the fuse as described below.

The inverting input of comparator logic 184 is coupled to additional circuitry (FIG. 11) (e.g., a resistor 117 (e.g., 2.7K Ohm) connected in series with pin 1, a resistor 136 (e.g., 270 Ohm) disposed between the inverting input and microprocessor 190, a capacitor 111 (e.g., 0.1 μf) connected between the inverting input and a ground potential, a diode 195 connected between the inverting input and the supply voltage, and diodes 109, 115 connected in parallel between pins 1 and 2) to enable proper operation, protect the circuit from damage in the event an external voltage is applied to pins 1 and 2 and/or to provide filtering to prevent a response to noise. The non-inverting input of comparator logic 184 is coupled to a reference voltage (e.g., 2.5V DC). This potential may be produced by a voltage divider circuit including resistors 126, 128 (e.g., each 2.7K Ohms) arranged in series and coupled to the supply voltage (e.g., 5V DC).

Pin 2 is connected to an output of microprocessor 190 with a resistor 193 (e.g., 2.7K Ohm) disposed between the pin and the microprocessor output. The microprocessor output provides either a ground potential or a high impedance state to detect solution or leaks within the drape container as described below. Pin 2 is further coupled to a diode 118 disposed between the pin and a ground potential. These items enable proper operation, protect the circuit from damage in the event an external voltage is applied to pins 1 and 2 and/or to provide filtering to prevent a response to noise.

Comparator logic 184 determines the presence of drape container conditions by comparing the potential of pin 1 (coupled to the inverting input) to the reference voltage (e.g., 2.5V DC). In order to detect the presence or absence of solution within the drape container, the microprocessor provides a ground potential at the microprocessor output coupled to pin 2. The configuration of the condition circuit basically forms a voltage divider circuit from the supply voltage (e.g., 5V DC) through resistor 191 (e.g., 100K Ohms), solution between pins 1 and 2 and resistor 193 (e.g., 2.7K Ohms) to the ground potential. The potential of pin 1 is based on the combined resistance of the solution and resistor 193. If the resistance between pins 1 and 2 (e.g., of the solution) is below 97.3K Ohms indicating the presence of solution in the basin, the voltage divider circuit produces a voltage on pin 1 less than the reference voltage (2.5V DC) since the combined resistance of the solution and resistor 193 (e.g., 2.7K Ohms) is less than the resistance of resistor 191 (e.g., 100K Ohms). Accordingly, comparator logic 184 produces a high level signal to indicate the presence of solution. The microprocessor subsequently provides a signal to illuminate green diode 147 and actuate power switch circuitry 196 to enable heater 70 and temperature controller 38 in response to the signal indicating the presence of solution without a leak in the drape container.

Power switch circuitry 196 includes an optocoupler 150 and a triac 154. The triac is connected between conductors 160, 162 that provide signals to temperature controller 38, and has a gate terminal coupled to an output of the optocoupler. Another optocoupler output is coupled to circuit board pin 3 and, hence, to green diode 147 disposed between circuit board pins 3 and 6, while a resistor 158 (e.g., 180 Ohm) is connected between pin 3 and the optocoupler. An output of the microprocessor is connected to an input of the optocoupler to drive the power switch circuitry in response to the presence of solution without a leak in the drape container as described above. A resistor 152 (e.g., 22 Ohms) is connected to an optocoupler output and in series with the triac. A low level logic signal produced by the microprocessor provides a ground that enables the optocoupler input to receive appropriate current to produce outputs that drive the triac. Thus, the low level logic signal from the microprocessor enables actuation of the green diode and triac to indicate the presence of solution without a leak in the drape container and to enable the heater and temperature controller, respectively. The triac basically enables and provides signals to temperature controller 38 to control actuation of the heater as described above.

When solution is absent from the basin, the voltage divider circuit basically forms an open circuit between pins and 1 and 2. Accordingly, pin 1 has the potential of the supply voltage (e.g., 5V DC) that exceeds the reference voltage (e.g., 2.5 V DC), and comparator logic 184 produces a low level signal to indicate the absence of solution. The microprocessor provides a signal to actuate yellow diode 149 in response to the comparator signal indicating the absence of solution and a leak within the drape container. The yellow diode is disposed between circuit board pins 4 and 7 with a resistor 170 (e.g., 270 Ohm) connected between pin 4 and the microprocessor output. A low level logic signal produced by the microprocessor provides a sufficient voltage differential to enable pin 7 connected to a supply voltage (e.g., 5V DC) to illuminate yellow diode 149.

In order to detect leaks, the microprocessor provides a high impedance state at the microprocessor output coupled to pin 2. This effectively removes resistor 193 from the voltage divider circuit path. When a leak is present in the drape, the solution creates the voltage divider path from the supply voltage (e.g., 5V DC) through resistor 191 (e.g., 100K Ohms), pin 1 and the solution to a ground potential (e.g., the basin). In this case, the potential of pin 1 is based on the resistance of the solution. If the resistance between pins 1 and 2 (e.g., of solution) is below 100K Ohms indicating the presence of a leak, the voltage divider circuit produces a voltage on pin 1 less than the reference voltage (2.5V DC) since the resistance of the solution is less than the resistance of resistor 191 (e.g., 100K Ohms). Accordingly, comparator logic 184 produces a high level signal to indicate the presence of a leak. Microprocessor 190 produces an oscillating output or pulse train responsive to the output of the comparator logic. The oscillating output of the microprocessor is coupled to a reference terminal of a speaker 197 and to pin 5 for actuating red diode 151. A resistor 143 (e.g., 270 Ohm) is disposed between pin 5 and the oscillating output, while a speaker positive terminal is connected to a supply voltage (e.g., 5V DC). The oscillating output is in the form of a pulse train that provides periodic low level logic signals. The low level signals provide a sufficient voltage differential to enable the supply voltages of the red diode (e.g., 5V DC of pin 8) and speaker (e.g., 5V DC of the speaker positive terminal) to drive those devices. Thus, the microprocessor produces a pulse train that enables the diode to flash and the speaker to beep at rates proportional to the pulse train frequency when a leak is present in the drape container.

The microprocessor further indicates and detects prior use of a drape by sensing and altering the state of fuse 89 as described below. In particular, the microprocessor initially detects the presence of fuse 89 of a drape prior to system operation. Once the fuse is detected, the microprocessor provides a signal of sufficient current to disable the fuse, thereby preventing subsequent detection of an enabled fuse and re-use of that drape with the system. The microprocessor further detects the presence of the fuse after disablement prior to initiating system operation to prevent a user from bypassing the fuse circuit with a conductive element (e.g., coin, etc.).

Comparator logic 184 may be further utilized to detect the presence of an enabled fuse 89. In particular, a voltage divider circuit is basically formed and includes resistor 186 (e.g., 180 Ohms), pin 1 and fuse 89. The resistor and fuse serve as the resistive elements for the voltage divider arrangement. Microprocessor 190 provides an initial supply voltage (e.g., 5V DC) to flow from the microprocessor through resistor 186, pin 1 and the fuse to a ground potential. When a drape is provided with a disabled fuse (e.g., an attempt to re-use the drape), the voltage divider effectively includes an open circuit between the pin and ground, and pin 1 has the potential of the supply voltage (e.g., 5V DC). Since pin 1 (e.g., 5V DC) exceeds the reference voltage (e.g., 2.5 V DC), comparator logic 184 produces a low level signal to indicate the disabled state of the fuse. The microprocessor prevents system operation until a drape with an enabled fuse is provided for use with the system.

If the resistance between pin 1 and ground (e.g., resistance of the fuse) is below 180 Ohms indicating the presence of the fuse, the voltage divider circuit produces a voltage on pin 1 less than the reference voltage (2.5V DC) since the resistance of the fuse is less than that of resistor 186 (e.g., 180 Ohms). Comparator logic 184 produces a high level signal to indicate the presence of the fuse. The microprocessor subsequently disables the fuse as described below and initiates system operation in response to verifying the disabled state of the fuse. The current through the fuse may be derived from the supply voltage and resistance (e.g., 5V/180 Ohms=0.027 Amps).

In order to disable the fuse, microprocessor 190 is coupled to and provides a signal to control switch 194. Basically, the microprocessor provides a ground potential to provide a path for the supply voltage (and current) to the gate of transistor 199. This enables the transistor to conduct and places the switch in a closed state. Current subsequently flows through the switch to pin 1, thereby disabling fuse 89. The current for disabling the fuse is derived from the supply voltage divided by the resistance (e.g., 5V/(3.9 Ohms of resistor 198+the external resistance)). The microprocessor subsequently detects the disabled state of the fuse in the manner described above prior to enabling system operation in order to prevent users from bypassing the fuse circuit via a conductive element (e.g., inserting a conductive element to emulate the presence of the fuse).

The condition circuit basically controls system operation in response to detected drape container conditions. The circuit is arranged to enable signals from the microprocessor to selectively facilitate a particular action (e.g., illuminate the red diode and speaker, enable the green diode and heater, illuminate the yellow diode, etc.) in response to the occurrence of corresponding conditions for that action. In other words, a particular action is initiated by the condition circuit in response to the occurrence of corresponding conditions, while remaining actions are disabled. Thus, the green diode and heater are enabled by the condition circuit in response to the presence of solution without a leak in the drape container, and are disabled during occurrence of other drape container conditions (e.g., a leak or no solution within the drape container). Enablement and disablement of the yellow diode and red diode and speaker are facilitated in a similar manner with respect to their corresponding conditions. The condition circuit and/or circuit board may further include circuitry to record the time and/or date when the system or heater is enabled and disabled or any other information. The stored information may be retrieved for hospital records or to assist in evaluating system performance.

Figure 12:
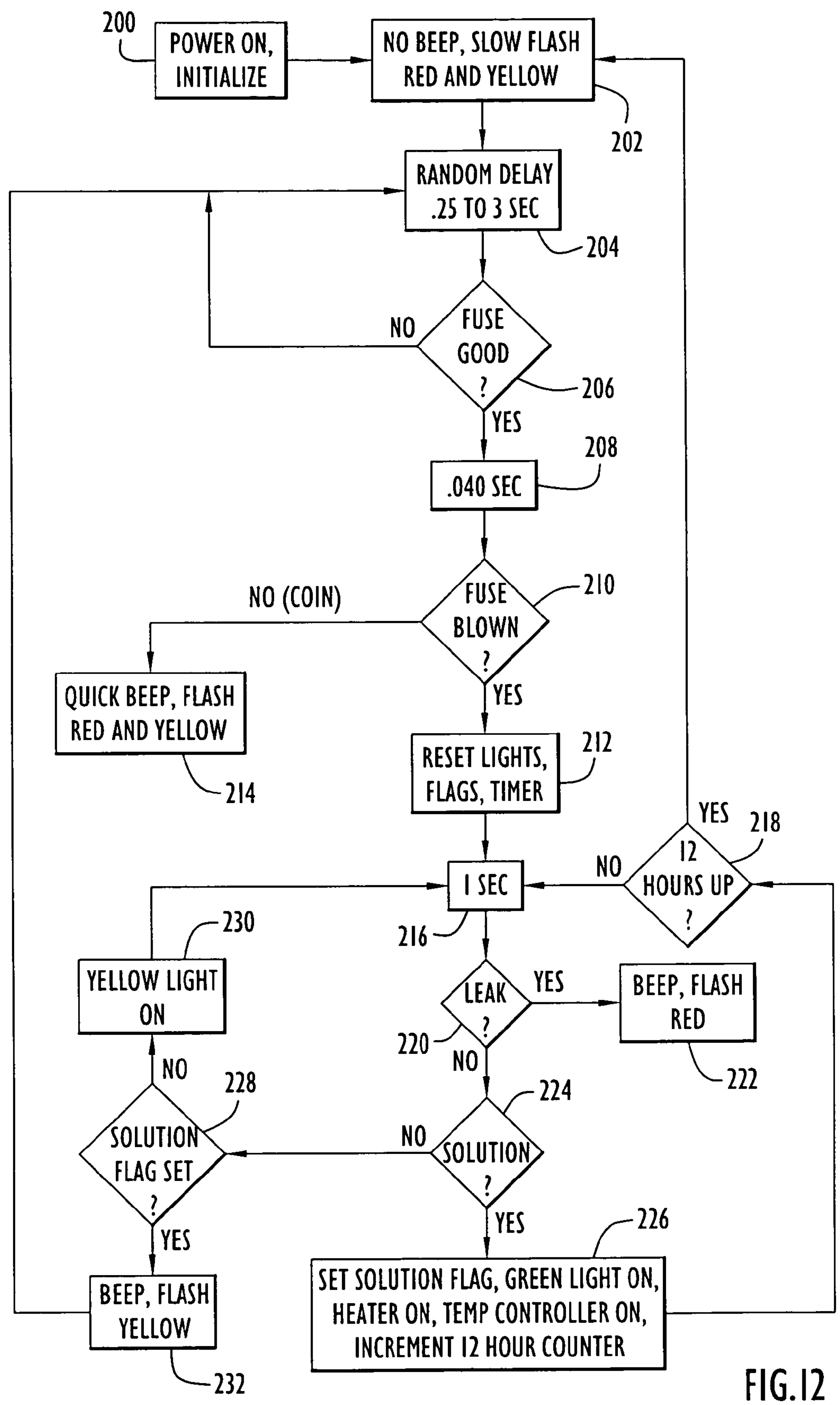
FIG. 12 is a procedural flow chart illustrating operation of the thermal treatment system of FIG. 1.

The manner in which the condition circuit operates is described with reference to FIGS. 11-12. Initially, the system is enabled and initialized at step 200. The microprocessor flashes red and yellow diodes 149, 151 at step 202. This may be accomplished by the microprocessor providing an output signal in the form of a pulse train to flash those diodes. The microprocessor subsequently determines a random delay interval, preferably in the range of 0.25 to 3.0 seconds, and waits for expiration of the interval at step 204 prior to detecting the presence of fuse 89. This random delay prevents users from bypassing the safety feature of the drape (e.g., using a new drape to initiate system operation, while employing a different drape for the medical procedure, etc.) as described below. The microprocessor provides a supply voltage (e.g., 5V DC) to resistor 186 to detect the presence of an enabled fuse as described above. If the fuse is present, the voltage divider arrangement enables pin 1 to have a voltage less than that of the reference voltage (e.g., since the resistance of fuse 89 is less than that of resistor 186) as described above, and comparator logic 184 produces a high level signal. When the fuse is disabled, the voltage divider arrangement enables pin 1 to have the potential of the supply voltage (e.g., 5V DC) as described above. In this case, pin 1 exceeds the reference voltage and comparator logic 184 produces a low signal. If the fuse is disabled as determined at step 206, the microprocessor repeatedly determines a new random delay interval and detects the presence of an enabled fuse as described above until an enabled fuse is sensed. The microprocessor basically prevents system operation until a drape with an enabled fuse is provided for system use. These conditions further prevent use of the system without a drape or with drapes (e.g., plain drapes, etc.) lacking the sensing device and/or fuse. The random nature of the interval inhibits users from initially using a drape with a fuse and subsequently substituting the initial drape with previously used or non-compatible drapes since users would not know the appropriate time to switch the drapes to bypass the sensing.

When a fuse is detected as determined at step 206, the microprocessor waits for a predetermined interval (e.g., 0.04 seconds) at step 208 prior to disabling the fuse. The microprocessor provides a signal to fuse 89 of sufficient current to render the fuse inoperable as described above. Once the signal has been sent, the microprocessor detects the presence of a disabled fuse in the manner described above to ensure that a user is not attempting to bypass a disabled fuse with a conductive element (e.g., using a coin or other conductor to provide a conductive path and simulate the presence of an enabled fuse). If the microprocessor receives a signal from comparator logic 184 indicating an enabled fuse after fuse disablement as determined at step 210, this indicates use of a conductive element in place of the fuse in an attempt to bypass the system. Accordingly, the microprocessor produces a quick beep from speaker 197 and flashes yellow and red diodes 149, 151 at step 214 to notify personnel of this condition. This continues until system reset, where a new drape may be provided for system use.

If the fuse is confirmed to be disabled as determined at step 210, the microprocessor performs an initialization at step 212 (e.g., resets diodes, flags, timers, etc.) and waits for a predetermined interval (e.g., one second) at step 216 prior to detecting drape container conditions.

The microprocessor detects the presence of a leak at step 220. Initially, microprocessor 190 places an output coupled to resistor 193 in a high impedance state as described above, where pin 1 has the potential of the supply voltage. When a leak occurs, a conductive path is formed from the supply voltage through resistor 191, pin 1 and the solution to a ground potential (e.g., the basin). This forms a voltage divider circuit (e.g., from the supply voltage through resistor 191 and pin 1 to ground), where the lesser resistance of the solution relative to resistor 191 enables the potential of pin 1 to be reduced below the comparator logic reference potential (e.g., 2.5V DC) as described above, thereby causing comparator logic 184 to produce a high level logic signal. When a leak is present as determined at step 220, the microprocessor detects the comparator signal and illuminates red diode 151 and actuates speaker 197 to provide an audio leak indication at step 222.

When a leak is absent, the microprocessor detects the presence of solution in the basin at step 224. Initially, microprocessor 190 places an output coupled to resistor 193 at a ground potential. In the event that solution is present in the drape container, a conductive path is formed from the supply voltage through resistor 191, pin 1, the solution, pin 2 and resistor 193 to the ground potential forming a voltage divider as described above. The voltage divider provides pin 1 with a voltage less than the reference voltage (e.g., 2.5V DC) since the combined resistance of the solution and resistor 193 (e.g., 2.7K Ohms) is less than the resistance of resistor 191 (e.g., 100K Ohms). Accordingly, the output of comparator logic 184 is high to indicate the presence of solution. When solution is absent from the drape container, no current flow exists between the drape electrodes and the voltage divider effectively includes an open circuit with pin 1 having the potential of the supply voltage. In this case, since the voltage applied to pin 1 (e.g., 5V DC) is greater than the reference voltage (e.g., 2.5V DC), the output of comparator logic 184 is low to indicate the absence of solution.

When solution is present as determined at step 224, the microprocessor detects the high comparator logic signal and sets a solution flag, illuminates green diode 147, actuates power switch 196 to enable the heater and temperature controller 38, and increments a counter or timer at step 226. The timer maintains a time interval for operation of the system (e.g., twelve hours, etc.). If the time interval expires as determined at step 218, the system resets to repeat the above process at step 202. Otherwise, the microprocessor waits for expiration of the time interval at step 216 and repeats the detection for leaks and solution.

If solution is absent from the drape container, the microprocessor detects the low comparator logic signal and determines the state of the solution flag at step 228. If the solution flag is set indicating the basin had solution, the microprocessor provides an audio beep indication to speaker 197 and flashes yellow diode 149 at step 232. This condition generally indicates placement of a new drape on the system (e.g., an old drape with solution is removed from the system and a new drape is placed on the system). The microprocessor subsequently waits for the random interval at step 204 and repeats the above process.

When the solution flag is not set indicating the basin has yet to receive solution, the microprocessor flashes yellow diode 149 at step 230. The microprocessor subsequently waits for expiration of the time interval at step 216 and repeats the detection for solution and leaks.

The condition circuitry may employ any conventional or other components with any desired electrical properties (e.g., resistance, capacitance, etc.) that can perform the above-described functions. The potential provided to electrodes 92 and/or 94 for detecting drape container conditions may be supplied in an intermittent manner to prevent the solution within the drape container from attaining a charge and affecting the potential across those electrodes which may cause erroneous detections. This may be accomplished by an oscillating power supply or via microprocessor 190. The reference voltage utilized by comparator logic 184 may be any suitable voltages. By way of example only, the reference voltage utilized by the comparator logic and/or the component electrical properties in the condition circuit may be derived from the properties of the solutions employed. Further, the reference voltage and/or electrical properties may be adjusted to account for objects placed in the basin. For example, placement of conductive objects (e.g., instruments, etc.) within the basin may establish a path for current flow between the conductive segments irrespective of the presence of solution, thereby enabling the condition circuit to indicate erroneous conditions. Accordingly, the reference voltage may be adjusted to differentiate between current flow initiated by solution and the current flow initiated by a conductive object. Alternatively, conductive objects may be utilized in combination with a stand disposed within the basin to elevate the objects above the conductive segments and basin floor in a manner similar to that disclosed in U.S. Pat. No. 6,087,636 (Faries, Jr. et al.).

In addition, the control circuitry may include devices to measure, record and/or provide a report (e.g., hardcopy or electronic form) of system conditions (e.g., time, date, temperature, leak indication, etc.). The report provides medical personnel documentation for their files on the heating characteristics. The primary information produced is the start date and start time of solution heating, the time interval the solution was heated and the temperature the solution attained during heating (e.g., partial or complete history of time and solution temperature). The solution temperature may be measured by sensor 272. For example, the report may include a graphical plot of solution temperature (e.g., time versus temperature) with indicators indicating the time of withdrawal of solution from the basin. The report may further include a variety of information (e.g., facility name and location, patient information, doctor information, type of procedure, type of solution and/or instruments being heated, amount of solution being heated, time of withdrawal of solution from the basin, etc.).

Referring back to FIG. 9, the control circuitry may further include a processor 110, a printer 120 and a communications module 180. These components may be implemented by any conventional or other components performing the functions described herein. Processor 110 is coupled to temperature controller 38 and detection circuitry 100 in order to receive information relating to the basin, liquid temperature, heater temperature and/or drape container conditions. The processor may receive any additional information (e.g., facility information, doctor information, patient information, solution information, instrument information, case information, etc.) from medical personnel or users via processor input devices (not shown). Alternatively, information may be entered by use of bar codes or Radio Frequency identification (RFID) via a bar code scanner or RFID reader 215. A bar code or RFID tag may indicate any desired information and be placed on any suitable items (e.g., drape, patient file or folder, patient tag or bracelet, etc.).

Processor 110 may further be coupled to sensors 217 and/or 272 to detect various conditions. For example, the system may detect withdrawal of sterile medium from the basin. In this case, sensors 217 may include a weight sensor disposed proximate the basin to detect a change (e.g., decrease) in weight of the basin, thereby indicating withdrawal of solution. RFID reader 215 may alternatively be utilized to detect removal of the sterile medium from the basin. In this case, the reader is disposed proximate the basin and utilized in conjunction with an RFID label disposed on a pitcher or other implement used to remove the sterile medium from the basin, where the reader detects manipulation (e.g., presence and absence) of the implement within the basin indicating withdrawal of sterile medium from the basin. Further, sensors 217 may include an optical sensor disposed within the basin to detect manipulation (e.g., presence and absence) of the implement within the basin indicating withdrawal of sterile medium from the basin.

Moreover, sensors 272 of electrode strip 95 may be in the form of a proximity or optical sensor to detect manipulation (e.g., presence and absence) of the implement within the basin indicating removal of sterile medium, or may be in the form of a Hall effect sensor and be utilized in conjunction with a magnetic tag disposed on the implement to detect the implement manipulation within the basin. In this case, electrodes coupled to the sensor may provide signals to corresponding pins of circuit board 52, where processors 110 and/or 190 may receive and process the electrode signals to determine conditions and/or provide the reports. In addition, the signals on electrodes 92, 94 may be affected by the fluid level in the basin, where processor 190 may detect the voltage or resistance of these electrodes (e.g., via circuit paths) to determine the occurrence of a change in fluid level (e.g., and hence, removal of sterile medium from the basin). Processor 110 may process this information for the reports.

Processor 110 further maintains the date, elapsed heating time and occurrence time of an event or condition (e.g., the time when a leak occurs, the time when instruments are inserted within the drape container, withdrawal of solution from the drape container, etc.). The processor may measure the elapsed time or record an occurrence time based on signals received from the temperature controller and/or detection circuitry. For example, the processor may initiate measurement of a time interval in response to the detection circuitry indicating solution within the drape container, and may store the elapsed and/or occurrence time in response to a leak or other condition. The processor may further measure elapsed time or record elapsed and/or occurrence time in response to medical personnel manually entering information on the processor input devices (e.g., start and stop keys).

The processor collects the appropriate information and arranges the information into a report. The report may be arranged in any fashion and include any desired information. Moreover, the report and/or information may be stored in a database or memory device (e.g., local memory, removable memory, card, disk, etc.) for later retrieval. In addition, the processor is coupled to a processor or system display 35 to display the elapsed (or running) time, report or any desired information to medical personnel. The information displayed may be selected via the processor input devices, or the display may include display controls (e.g., buttons, keys, etc.). Display 35 may be disposed on the cabinet (FIG. 1) at any desired location.

The processor is further coupled to printer 120 and communications module 180 in order to provide information to a user. The printer basically provides a report in hardcopy form. The processor may control the printer to produce the report at specified times (e.g., termination of heating, at particular times of day, after a particular quantity of uses, etc.) or in response to requests from medical personnel via processor input devices (e.g., print key). The printer may print the report on any desired hardcopy medium. Preferably, the printer places the information onto a label that is attached to a medical file. The information may be printed during or after the solution heating, or be stored on a memory device and printed at a desired time as described above. The printer may further provide additional copies of the report in response to user requests, or a medium automatically creating duplicates may be utilized (e.g., carbon-less paper, etc.). Cabinet 31 may include a slot (not shown) to provide the printed report to a user. However, the slot may be defined at any desired location. Since the cabinet is under the drape adjacent the non-sterile drape side (e.g., the cabinet is non-sterile), the printed report is typically retrieved from the cabinet after completion of the medical procedure (e.g., when the drape is discarded) to preserve sterility. The system may provide a power-off delay to enable printing of reports and/or labels for a limited time interval after power down of the system (e.g., actuation of power switch 37).

Communications module 180 enables the report to be provided in electronic form. This module basically facilitates communication with other devices for transference or downloading of the report to those devices. For example, the information may be downloaded or transmitted over a network or other communications medium to another device (e.g., PDA, computer, another thermal treatment system, etc.) for viewing, storage and/or printing. Moreover, the communications module may facilitate retrieval of information (e.g., patient information, facility information, doctor information, solution information, instrument information, etc.) from a database or other source for the report.

Operation of the thermal treatment system with the present invention drape is described with reference to FIGS. 1 and 9-11. Initially, drape 17 is placed over the top surface of the thermal treatment system and disposed in basin 33 to form a drape receptacle. Electrode strip 95 of the drape is coupled to receptacle 49 to connect the drape to the detection circuitry to facilitate detection of drape container conditions. Power switch 37 is actuated and the detection circuitry detects the presence of an enabled fuse. Once an enabled fuse is detected, the detection circuitry disables that fuse to prevent re-use of the drape with the system and further detects the fuse status to ensure the fuse has actually been disabled. After the fuse disablement is confirmed, the detection circuitry senses the absence of solution and a leak within the drape container in the manner described above. A corresponding diode may be illuminated to indicate this condition, while thermal treatment of the basin may be disabled.

A sterile medium is disposed within the drape receptacle and a desired temperature for the medium is entered into the system by the user via controller 38. The sterile medium forms a conductive path between electrodes 92, 94 that affects the resistance (or voltage) along a circuit path within the detection circuitry as described above. The detection circuitry senses the change indicating the presence of solution without a leak in the drape container, and may illuminate a corresponding diode. Temperature controller 38 is subsequently enabled and controls thermal treatment of the basin.

When a leak occurs within the drape container, the resistance (or voltage) along the circuit path changes as described above. The detection circuitry senses the change indicating a leak within the drape container and may disable thermal treatment of the basin. A corresponding diode may be illuminated to indicate this condition. Further, processor 110 may receive information from the temperature controller, sensors 217, 272 and/or detection circuitry to record the elapsed and/or occurrence time as described above.

Processor 110 may receive appropriate information for a report from the temperature controller, sensors 217, 272, detection circuitry and/or processor input devices at any time (e.g., before, during or after the heating session). The processor arranges the information into a desired report as described above. The report may be produced by printer 120 or transmitted to another device via communications module 180 as described above. The report may be generated in response to termination of a session (e.g., indicated by signals received by processor 110 from the temperature controller and/or detection circuitry) or a request by medical personnel (e.g., via processor or other input devices).

Figure 13:
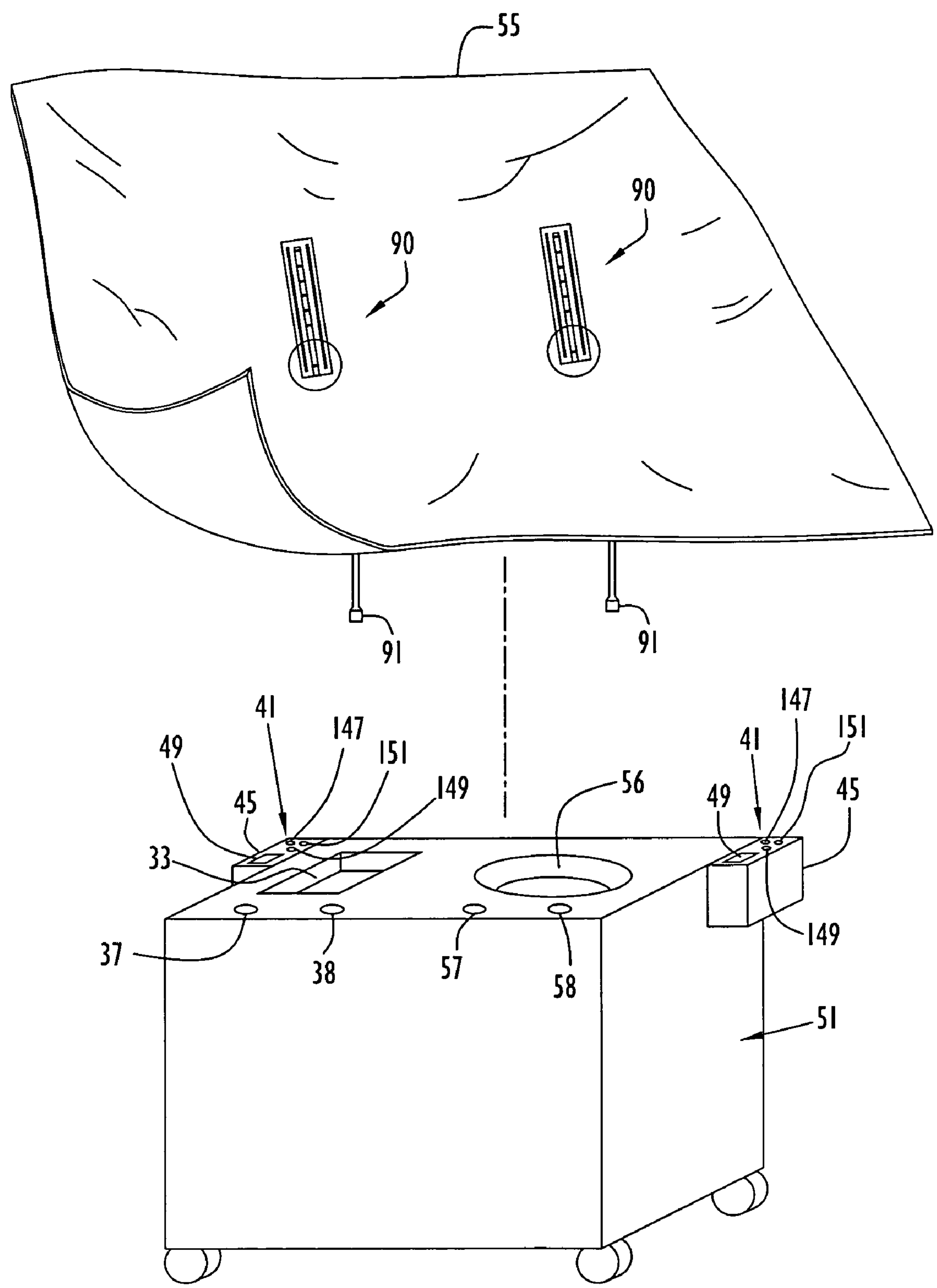
FIG. 13 is an exploded perspective view of a surgical drape including plural sensing devices and disposed over a plural basin thermal treatment system according to the present invention.

It is to be understood that the present invention may be employed for thermal treatment systems including a plurality of basins that either heat or cool the sterile medium. An exemplary plural basin system and corresponding drape according to the present invention are illustrated in FIG. 13. Specifically, the plural basin system includes an integral assembly 51 including warming basin 33 and a substantially circular cooling basin 56 to thermally treat sterile liquid. The system may alternatively be in the form of an integrated table top unit (with or without a stand), or separate individual table top units (with or without a stand) similar to the unit described above for FIG. 1. The plural basin system includes power switches 37, 57 and controllers 38, 58 to control operation of the warming and cooling basins, respectively. The assembly further houses the heating and refrigeration devices and control circuitry (not shown) for the individual basins to thermally treat those basins and liquid contained therein as described above.

A drape 55, substantially similar to drape 17 described above, is placed over the system and within each basin to form a drape receptacle therein as described above. Sensing devices 90 are affixed at appropriate locations on the drape in the manner described above for insertion within a corresponding basin to detect drape container conditions within that basin. Electrode signals are conveyed from each sensing device disposed within a basin to a corresponding individual condition circuit associated with that basin to determine drape container conditions and provide signals to control the basin in substantially the same manner described above. The assembly may further include a wiring housing 45 associated with each basin to transfer signals between that housing and a corresponding individual condition circuit in substantially the same manner described above. Each wiring housing may include a receptacle 49 to receive a corresponding connector 91 of the associated drape sensing device. Alternatively, the receptacles may be disposed on a top surface of the assembly adjacent a corresponding basin in substantially the same manner described above. Each wiring housing typically includes diodes 147, 149, 151 to indicate drape container conditions within a corresponding basin. The individual basins each basically function in substantially the same manner as the single basin system described above, where the plural basins may be individually controlled or collectively controlled (e.g., all basins enabled or disabled) in response to drape container conditions.

It will be appreciated that the embodiments described above and illustrated in the drawings represent only a few of the many ways of implementing a system and method of detecting fluid and leaks in thermal treatment system basins.

The warming, cooling and plural basin systems and their corresponding cabinets, assemblies or housings may be of any shape or size and may be constructed of any suitable materials. The systems may include an integral housing or individual units. Further, the systems may include a housing for free standing operation, or be in the form of table or counter top units. The plural basin system may include any quantity of heating and/or cooling basins in any combinations. The basins of the systems may be of any shape or size, may be constructed of any suitable thermal conducting materials (e.g., stainless steel, etc.) and may be disposed at any suitable locations on or within the housings. The systems may include any conventional or other heating and/or refrigeration units to thermally treat the sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.-160° F.). The heater may be of any quantity (e.g., at least one), shape or size, and may include any configuration (e.g., strips, bars, segments, etc.) that covers the entirety or any portion of a basin. The heater may be attached to a basin via any conventional or other fastening techniques (e.g., any type of adhesives, brackets, etc.). In addition, the heater may be implemented by any conventional or other type of heater or heating element (e.g., heating coils, etc.) that may be disposed on or proximate a basin at any suitable locations.

The cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor may be implemented by any quantity of any conventional or other temperature sensing device (e.g., infrared, RTD, etc.), may be disposed at any location on, within or proximate a basin or within the systems to measure temperature of any desired items (e.g., basin, heater or cooler, liquid, etc.). The measured item temperatures may be utilized for display, reports, system operational control or any other desired application. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The wiring housing may be of any quantity, shape or size, may be constructed of any suitable materials, and may be disposed at any suitable locations on the systems. The wiring housing and/or systems may include any suitable conductors or other medium (e.g., wireless, fiberoptics, etc.) to transfer signals between system components. The wiring housing or system may include any quantity of any type of receptacle disposed at any suitable location on the wiring housing or systems to interface the drape. The receptacle may be of any quantity, shape or size and include any quantity of receptacles to interface the drape. The receptacles may include any quantity of any suitable contact (e.g., clamp, terminal, etc.) to transfer signals with the drape.

The wiring housing may include any quantity of any type of indicator (e.g., audio, speech synthesis, LED, display screen with text or images, speaker, etc.) to indicate the drape container status. The indicator may be disposed on the wiring housing or systems at any suitable locations. The diodes may be of any quantity or color, may be disposed at any suitable locations on the wiring housing or systems and may be illuminated in any desired fashion or pattern (e.g., flashing, continuous illumination, etc.). A drape container or other condition may be associated with any quantity of any diodes of any color (e.g., the same or different colors in any desired combinations, etc.).

The drape may be of any size or shape, may be constructed of any suitable materials, and may include any suitable electrical or other properties (e.g., conductance/resistance, nonconductive, conductive, etc.) compatible with the sensing device. The drape is preferably transparent or translucent to facilitate manipulation of controls through the drape; however, the drapes may have any degree of transparency (e.g., including opaque). The drape may be manipulated in any fashion with any portions of the drape serving as a drape receptacle within a corresponding basin. The drape may be of sufficient size to accommodate and form drape receptacles within any quantity of thermal treatment system basins.

The sensing device may include any quantity of electrodes or electrode strips disposed at any suitable locations on a drape. The electrodes may be constructed of any suitable conductive materials (e.g., metallic ink, wires, strips, etc.). The electrode strip may be of any shape or size, and may be constructed of any suitable materials. The electrodes may be fastened to the strip at any suitable locations via any conventional or other fastening techniques. The strip may include any quantity of any conventional or other sensors (e.g., temperature, humidity, optical, Hall effect, magnetic, etc.) to detect any suitable conditions (e.g., temperature, fluid level, withdrawal of solution, etc.). The sensors may be coupled to any quantity of electrodes on the strip to transfer signals. The pouch may be of any quantity, shape or size, may be constructed of any suitable materials, may contain any portions of the electrodes or electrode strip and may be fastened to the drape at any suitable locations via any conventional or other fastening techniques. The flap may be of any quantity, shape or size, may be attached to the drape at any suitable locations via any conventional or other fastening techniques to form the pouch and may be constructed of any suitable materials. The seams may be disposed on the flap at any suitable locations in a continuous or intermittent fashion to attach the flap to the drape to form the pouch. The flap may include any quantity of openings or slots of any shape or size disposed in any suitable locations on the flap or pouch and arranged in any fashion to enable liquid within the drape container to contact the electrodes. Alternatively, the sensing device or electrode strip may be attached to the drape (e.g., without the pouch) via patches or any other securing mechanisms (e.g., adhesives, welding, etc.) to sense drape container conditions.

The drape opening may be of any quantity, shape or size and may be defined in the drape at any suitable locations (e.g., drape portions within the basin, on the top surface, near the controller or wiring housing, along the cabinet side walls, etc.). The patches may be of any quantity, shape or size, may be constructed of any suitable materials and may be disposed at any suitable locations on the drape. The drape may include any quantity of openings and corresponding patches disposed on or attached to either or both of the sterile and non-sterile drape surfaces. Any patch portions may be attached to the drape, where the bend or fold may be disposed at any location and the transverse patch sections may extend at any angle or orientation. Alternatively, the patches may lay flat against the drape with the strip extending through the patches or from a peripheral patch edge. Further, any quantity of patches may be utilized to seal the opening and/or strip, where the patches may be disposed at any locations relative to the drape opening (e.g., same or opposing sides, any angular displacement, etc.) and be attached to each other and/or the drape.

The patches may be secured or attached to any portions of each other, any portions of the strip and/or any portions of the drape (e.g., at any locations, the entirety or any portion thereof, etc.) via any conventional or other techniques (e.g., adhesives, heat welding, pressure, etc.). The drape may include any quantity of sensing devices for a corresponding basin where the sensing device signals may be combined in any fashion (e.g., at least one device detecting liquid, combined logically (e.g., AND, OR, etc.), etc.) to determine occurrence of drape container conditions (e.g., solution or leaks present).

The sensing device plug (e.g., rear panel, projection, etc.) may be of any shape or size and may be constructed of any suitable materials. The plug may be implemented by any conventional or other plug or connector where the electrode traces, fuse and/or sensors may be disposed at any locations on the plug or strip in any arrangement. Alternatively, the electrode strip or other objects may traverse a drape peripheral or other edge (e.g., without being disposed through the drape) to extend between the sterile and non-sterile drape surfaces. The plug may be received within the receptacle in any manner enabling transference of signals.

The plug may alternatively include a microprocessor or chip to process electrode signals and control the thermal treatment system (e.g., indicators, heater or any other devices). The microprocessor may generate the appropriate control signals to control basin thermal devices and various indicators in accordance with the determined conditions. In addition, the microprocessor may maintain use information for the drape and indicate prior use to the thermal treatment system to prevent system operation.

The fuse may be implemented by any type of electrical, mechanical or other device (e.g., transistor, fuse, switch, relay, optical device, audio device, electromechanical device, etc.) selectively controlled to disrupt, disable or alter characteristics of the electrical or other path (e.g., optical, wired, radio or wireless, audio, etc.). Alternatively, the fuse may be implemented by any device accessible by the microprocessor and including plural states to indicate sterility or prior use of the item (e.g., memory, optical indicators (e.g., LEDs or other devices with on/off states), etc.). The fuse may be of any quantity, shape or size, may include any current and/or voltage thresholds and may be accompanied by any additional circuitry (e.g., resistors, capacitors, inductors, switches, transistors, etc.) for a particular application. The fuse may be constructed of any materials (e.g., glass fuse, thin painted metallic line, etc.). The status and disablement signals may be of any quantity or magnitude sufficient to test the fuse status or disable the fuse (e.g., these signals may be of any voltage or current types or levels (e.g., digital, analog, AC, DC, volts, amps, any fractions of volts or amps, etc.)). The microprocessor may transmit the status and disablement signals in any fashion and in response to any desired conditions or at any desired time intervals (e.g., the status signals may be sent periodically, the disablement signal may be transmitted at any desired time interval after transmission of a status signal, etc.).

Drape container conditions may be determined based on any desired electrical or other parameters or characteristics (e.g., potential or voltage, current, resistance, etc.) of any quantity of electrodes and/or from the sensors coupled thereto. The parameters may be measured at any suitable locations (e.g., at any locations along each electrode, between the electrodes, between the electrodes and basin, at the basin, between the electrodes and detection circuitry, within the detection circuitry, etc.). In addition, the presence of the drape may be detected based on the connection (or lack thereof) of the drape electrodes to the thermal treatment system (or detection circuitry) to control system operation (e.g., disable thermal treatment of the basin in the absence of a drape).

The control circuit may be disposed within the systems at any suitable locations and may be implemented by any conventional or other circuitry components arranged in any desired fashion to perform the described functions. The systems may be powered by any conventional or other power source (e.g., AC, DC, wall outlet jack, batteries, etc.). The power supply and other components may be coupled via any conventional or other connectors for transferring signals. The power cord may be implemented by any conventional or other cord or cable and be configured to accommodate any desired power signals. The thermostat may be implemented by any conventional switching type or limiting devices, such as a high limit thermostat, and may be disposed at any suitable location within the systems.

The detection circuitry may be disposed within the system at any suitable locations and may include any quantity of conventional or other components arranged in any desired fashion to perform the functions described herein. The detection circuitry may utilize any suitable reference potentials to detect solution, leaks or any other conditions. The electrical connections may include any quantity of components (e.g., power cord, fuses, conductors, connectors, power supply, circuit board, diodes, etc.) arranged in any desired fashion, where each component may be implemented by any conventional or other component performing the described function. The temperature controller may be implemented by any conventional or other temperature controller and include any desired devices for entering a temperature (e.g., buttons, keypad, etc.). The temperature controller may control the heater to any desired temperature range, and may utilize any quantity of set points (e.g., maximum and/or minimum, etc.). The basin power switches of the systems may be implemented by any conventional or other switching device, while surge fuses may be implemented by any conventional fuse or other limiting device and may be configured for any current or voltage levels to protect the circuitry.

The circuit board housing the condition circuit may include any quantity of terminals or pins each associated with any desired signals or portion of the condition circuit. The circuit board may include any quantity of indicators disposed at any suitable locations to indicate the occurrence or status of any desired circuit portion or condition. The power supply may be implemented by any conventional or other power supply or source and provide any desired power signals, and may include any type of conventional or other receptacle for receiving any type of plug or connector. The diodes or other indicators may be connected to the circuit board pins in any desired fashion. The circuit board may house the condition circuit and/or any other desired system circuitry. Further, the circuit board may include devices to record any types of information relating to system operation for subsequent retrieval and analysis (e.g., date and time of thermal treatment disablement and enablement, etc.).

The condition circuit may include any quantity of conventional or other components arranged in any desired fashion to perform the functions described herein. The microprocessor may be implemented by any conventional or other microprocessor or controller. The comparator may be implemented by any conventional or other comparators or comparing devices (e.g., hardware and/or software) and may utilize any suitable reference potentials to detect solution, leaks or any other conditions. The microprocessor may produce oscillating outputs (e.g., pulse trains, etc.) at any desired frequency and drive any type of device (e.g., speaker, speech synthesis, diode, etc.) to indicate the presence of a condition, while the indicator devices may alternatively be driven by any type of circuitry or mechanism. The speaker may be implemented by any conventional or other speaker or audio device and may provide any suitable audio indication (e.g., beep at any suitable periodic interval, continuous audio output, etc.).

The triac may be implemented by any conventional or other triac or relay type device to provide signals to thermal control circuitry for controlling thermal treatment of a basin. The condition circuit may include any conventional or other circuitry (e.g., resistors, capacitors, inductors, diodes, supply and ground potentials, etc.) arranged in any fashion and including any desired electrical characteristic values (e.g., resistance, potential, capacitance, etc.) to facilitate circuit operation. The condition circuit signals may include any desired logic or voltage levels. The optocoupler may be implemented by any conventional or other optocoupler or other circuitry to control the triac to provide signals to the thermal control circuitry.

The microprocessor of the detection circuit may employ any suitable delays (e.g., seconds, minutes, etc.) for disabling and checking the status of the fuse. The delays may be determined in any suitable manner (e.g., predetermined, random, based on drape container or other conditions, etc.). The microprocessor may further be implemented by or implement the temperature controller and/or report processor.

The plural basin system may include individual thermal control and detection circuitry associated with each basin to monitor drape container conditions and control basin operation. Alternatively, the plural basin system may include common thermal control and detection circuitry to control each basin in response to drape container conditions. The common circuitry may receive signals from each of the electrodes and control the basins individually or collectively in response to the drape container conditions. The common circuitry may process and combine the signals in any fashion (e.g., AND, OR, etc.) to determine conditions for controlling the basins.

The control circuitry may include devices to record any types of information relating to system operation for subsequent retrieval, analysis, display and reports (e.g., date and time of thermal treatment disablement and enablement, etc.). The processor may be implemented by any conventional or other microprocessor or controller and include any quantity of any desired input devices (e.g., buttons, keypad, etc.). The processor may receive information from any suitable devices (e.g., bar code scanner, RFID reader, etc.) disposed at any suitable locations on or within the system. The reader/scanner may be implemented by any quantity of any conventional or other devices, where the bar code, RFID or other tag may provide any desired information and be disposed at any suitable locations on the patient or an article (e.g., label, patient chart, patient garment, equipment, etc.). The processor may maintain the date, elapsed heating time and/or occurrence time of any event or condition (e.g., time when a leak occurs, time instruments inserted within drape container, etc.). The processor may measure the elapsed time or record an occurrence time for any desired condition. The processor may maintain the time information internally or utilize any desired external circuitry (e.g., a timer, etc.).

The processor may collect any desired information (e.g., start date and time of solution heating, the time interval the solution was heated, the temperature the solution attained during heating, partial or complete history of time and solution temperature measured at any desired time intervals, facility name and location, patient information, doctor information, type of procedure, type of solution and/or instruments being heated, amount of solution being heated, etc.) from any desired sources (e.g., detection circuitry, temperature controller, user, memory device, another computer or device, sensors, etc.). The sensors may be of any quantity or type (e.g., weight, optical, magnetic, etc.) and may be disposed within the cabinet at any suitable locations to measure any desired conditions (e.g., withdrawal of solution, solution temperature, etc.).

The reports may be arranged in any fashion and include any desired information. The report information may be arranged and/or presented (e.g., printed, displayed, etc.) in any desired formats (e.g., text, charts, graphs, etc.). The report and/or information may alternatively be stored in a local or remote database or memory device (e.g., local memory, removable memory, etc.) for later retrieval. The reports may include a pre-arranged format or may be programmable or selected by a user via processor input devices. The system, controller and processor displays may be of any quantity, shape or size, may be disposed at any location on and/or within the system (e.g., cabinet, wiring housing, etc.) or remote from the system, may be implemented by any conventional or other displays (e.g., LED, LCD, etc.) and may display any desired information. The information displayed may be selected via controller or processor input devices, or the display may include display controls (e.g., buttons, keys, etc.).

The printer may be implemented by any conventional or other printing device, may be local or remote, may serve any quantity of systems or other devices, and may produce reports on any desired medium (e.g., paper, labels, etc.). The reports may be printed at any specific time or in response to user entered information (e.g., a print command or key). The printer slot may be of any quantity, shape or size and may be disposed at any suitable location on the cabinet and/or wiring housing. The report may be printed at any desired time before, during or after system use, and may be retrieved from the system at any desired time or in any desired manner that preserves a sterile field (e.g., after completion of the medical procedure, after discarding the drape, times when a sterile field is not needed or being employed by the system, etc.). The power-off delay may be set to any desired interval (e.g., one minute, five minutes, etc.) and may enable use of any system components during that interval subsequent power down of the system.

The communications module may be implemented by any conventional or other communications device or module (e.g., modem, etc.) and may download or transfer an electronic form of the report to any desired device (e.g., PDA, computer, another thermal treatment or other system, etc.) at any specific time or in response to user entered information (e.g., transmit command or key). The systems may further be networked to enable retrieval of reports and/or information from a station coupled to the network. The printer and communications module may be disposed at any suitable locations on or within the system (e.g., on or within the cabinet, wiring housing, etc.) or remote from the system. Any desired information may be transmitted between the control circuitry components (e.g., temperature controller, detection circuitry, processor, printer, communications module, displays, etc.) via any conventional or other communications medium or protocols (e.g., hardwire, wireless, network, etc.). The processor may implement or be implemented by the temperature controller. The various sensors (e.g., temperature sensor 72, sensors 217, 272, etc.) may be coupled to the temperature controller, microprocessor and/or processor either individually or in any combination or fashion.

software for the temperature controller, plug microprocessor, detection circuit microprocessor for processing the electrode signals and report processor may be implemented in any desired computer language and could be developed by one of ordinary skill in the computer arts based on the functional descriptions contained herein. The controller, microprocessors and/or processor may alternatively be implemented by any type of hardware and/or other processing circuitry, and may be available pre-programmed for immediate use. The various functions of the controller, microprocessors and/or processor may be distributed in any manner among any quantity of software modules, processors and/or circuitry. The software, algorithms and/or processes described above and illustrated in the flow chart and diagrams may be modified in any manner and/or may perform operations in any order that accomplishes the functions described herein.

It is to be understood that the terms “top”, “bottom”, “front”, “rear”, “side”, “height”, “length”, “width”, “upper”, “lower” and the like are used herein merely to describe points of reference and do not limit the present invention to any particular orientation or configuration.

From the foregoing description, it will be appreciated that the invention makes available a novel system and method of detecting fluid and leaks in thermal treatment system basins, wherein a surgical drape includes a sensing device with a fuse to prevent re-use of the drape and to provide signals indicating drape container conditions to a thermal treatment system to facilitate control of system operation.

Having described preferred embodiments of a new and improved system and method of detecting fluid and leaks in thermal treatment system basins, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for detecting conditions within containers formed by surgical drapes during surgical procedures and controlling thermal treatment of said containers in response to said detected conditions, said system comprising:

a thermal treatment unit to thermally treat a sterile medium and including a basin;

a surgical drape, covering and substantially conforming to said basin, to serve as a drape container for said sterile medium;

a sensing device to detect drape container conditions including sterility of said drape, wherein said sensing device includes a status device and a plurality of conductors responsive to contact with said sterile medium to indicate conditions of said drape container, and wherein said status device includes a plurality of states with the state of said status device indicating said sterility of said drape;

a controller to operate said thermal treatment unit to control a temperature of said basin; and a detection unit to determine occurrence of said drape container conditions from signals from said sensing device to control said controller to operate said thermal treatment unit in accordance with said determined drape container conditions.

2. The system of claim 1, wherein at least two of said conductors are disposed on a sterile drape surface within said drape container.

3. The system of claim 2, wherein said status device is coupled to at least one of said conductors.

4. The system of claim 1, wherein said status device includes a fuse.

5. The system of claim 2, wherein said sensing device includes a strip with said plurality of conductors disposed thereon and a connector to couple said sensing device to said detection unit.

6. The system of claim 5, wherein said connector includes said status device and at least a portion of said plurality of conductors.

7. The system of claim 5, wherein said strip includes a temperature sensor coupled to at least one of said conductors to measure temperature of said sterile medium.

8. The system of claim 5, wherein said sensing device detects a change in a sterile medium amount within said drape container and further includes at least one of a weight sensor to measure a change in weight of said basin indicating said change in said sterile medium amount, an optical sensor to detect an implement within said basin altering said sterile medium amount, a proximity sensor to detect said implement within said basin altering said sterile medium amount, a Hall effect sensor to detect said implement within said basin altering said sterile medium amount and an RFID reader to detect an RFID label disposed on said implement to detect said implement within said basin altering said sterile medium amount.

9. The system of claim 1, wherein said sensing device includes a connector with a processor to provide signals to said detection unit to indicate at least one of said state and said drape container conditions.

10. The system of claim 6 further including:

a receptacle to receive said connector and couple said sensing device to said detection unit.

11. The system of claim 10, wherein said receptacle includes at least one contact to engage a corresponding conductor of said connector.

12. The system of claim 11, wherein each contact includes a plurality of arms separated to receive and engage a corresponding conductor therebetween.

13. The system of claim 1, wherein a first state of said status device enables an electrical path and indicates a sterile drape, and a second state of said status device disables said electrical path and indicates prior use of that drape, and said detection unit includes:

a status module to provide a status signal on said electrical path and detect characteristics of said electrical path to determine said state of said status device and ascertain said sterility of said drape.

14. The system of claim 13, wherein said status module determines a random time interval and provides said status signal and determines said status device state in response to expiration of that time interval.

15. The system of claim 13, wherein said detection unit further includes:

an element module to disable said electrical path by controlling said status device to enter said second state to indicate use of said drape in response to detection of characteristics indicating an enabled electrical path.

16. The system of claim 15, wherein said detection unit further includes:

a verification module to provide said status signal on said electrical path to said status device and verify placement of the status device in said second state, wherein detection of said status device in said second state indicates a sterile drape and detection of said status device in said first state indicates a used drape utilizing a conductive member with said status device in said second state.

17. The system of claim 1 further including a plurality of indicators to indicate drape container conditions, wherein said indicators are actuable in response to control signals generated by said detection unit in accordance with said determined occurrence of said drape container conditions.

18. The system of claim 1, wherein said drape container conditions further include at least one of a leak and the presence of said sterile medium within said drape container and said detection unit disables said thermal treatment unit in response to determining at least one of the presence of a leak, the absence of said sterile medium within said drape container and said status indicating a non-sterile drape.

19. The system of claim 1, wherein said drape container conditions further include at least one of a leak and the presence of said sterile medium within said drape container and said detection unit enables said thermal treatment unit in response to determining the presence of said sterile medium and absence of a leak within said drape container.

20. The system of claim 1, wherein said thermal treatment unit is operative to do at least one of heat and cool said sterile medium in said drape container.

21. The system of claim 1, wherein said drape includes a pre-formed container portion to form said drape container within said basin.

22. The system of claim 1 further including a processor to collect information relating to a surgical procedure and to generate a report including said collected information.

23. The system of claim 22 further including:

at least one of a bar code scanner and an RFID reader to provide information to said processor.

24. The system of claim 22 further including a printer to print a hardcopy of said report.

25. The system of claim 24, wherein said printer is enabled after system power down for a predetermined time interval.

26. The system of claim 22 further including a communications module to establish communications and transfer information with another device, wherein said processor generates said report in electronic form and said communications module transmits said report to said other device.

27. The system of claim 1, wherein said drape is formed of an electrically conductive material.

28. The system of claim 1, wherein said drape is formed of an electrically non-conductive material.

29. The system of claim 2, wherein said detection unit includes at least one circuit path coupled to said at least two conductors to receive signals from said sensing device to determine said drape container conditions, and wherein said detection unit provides power signals to at least one conductor in an oscillating fashion to prevent said sterile medium from attaining a charge.

30. The system of claim 2, wherein said drape includes a pouch to house said at least two conductors.

31. The system of claim 30, wherein said pouch is attached to said drape via intermittent seams.

32. The system of claim 8, wherein said strip includes at least one of said optical sensor, said proximity sensor and said Hall effect sensor each coupled to at least one of said conductors.

33. A device for detecting conditions within a basin of a thermal treatment system during surgical procedures and facilitating control of thermal treatment of said basin and sterile medium contained therein in response to said detected conditions, said device comprising:

a surgical drape to cover and substantially conform to said basin to serve as a drape container for said sterile medium; and a sensing device to detect drape container conditions including sterility of said drape, wherein said sensing device includes a status device and a plurality of conductors responsive to contact with said sterile medium to indicate conditions of said drape container, and wherein said status device includes a plurality of states with the state of said status device indicating said sterility of said drape.

34. The device of claim 33, wherein at least two conductors are disposed on a sterile drape surface within said drape container.

35. The device of claim 34, wherein said status device is coupled to at least one of said conductors.

36. The device of claim 33, wherein said status device includes a fuse.

37. The device of claim 33, wherein said sensing device includes a strip with said plurality of conductors disposed thereon and a connector to couple said sensing device to said thermal treatment system.

38. The device of claim 37, wherein said connector includes said status device and at least a portion of said plurality of conductors.

39. The device of claim 37, wherein said strip includes a temperature sensor coupled to at least one of said conductors to measure temperature of said sterile medium.

40. The device of claim 37, wherein said sensing device detects a change in a sterile medium amount within said drape container and said strip includes at least one of an optical sensor to detect an implement within said basin altering said sterile medium amount, a proximity sensor to detect said implement within said basin altering said sterile medium amount, and a Hall effect sensor to detect said implement within said basin altering said sterile medium amount, each coupled to at least one of said conductors.

41. The device of claim 33, wherein said sensing device includes a connector with a processor to provide signals to said thermal treatment system to indicate at least one of said state and said drape container conditions.

42. The device of claim 33, wherein said drape includes a pre-formed container portion to form said drape container within said basin.

43. The device of claim 33, wherein said sensing device detects drape container conditions further including at least one of the presence of said sterile medium in said drape container and a leak within said drape container.

44. The device of claim 33, wherein said drape is formed of an electrically conductive material.

45. The device of claim 33, wherein said drape is formed of an electrically non-conductive material.

46. The device of claim 34, wherein said drape includes a pouch to house said at least two conductors.

47. The device of claim 46, wherein said pouch is attached to said drape via intermittent seams.

48. A system for detecting conditions within containers formed by surgical drapes during surgical procedures and controlling thermal treatment of said containers in response to said detected conditions, said system comprising:

a thermal treatment unit to thermally treat a sterile medium and including a basin;

a surgical drape, covering and substantially conforming to said basin, to serve as a drape container for said sterile medium;

a sensing device including a plurality of conductors with at least two of said conductors disposed on a sterile drape surface within said drape container and responsive to contact with said sterile medium to indicate conditions of said drape container;

a controller to operate said thermal treatment unit to control a temperature of said basin; and a detection unit to determine occurrence of said drape container conditions from signals from said sensing device to control said controller to operate said thermal treatment unit in accordance with said determined drape container conditions, wherein said detection unit includes at least one circuit path coupled to said at least two conductors to receive signals from said sensing device to determine said drape container conditions, and wherein said detection unit provides power signals to at least one conductor in an oscillating fashion to prevent said sterile medium from attaining a charge.

49. A device for detecting conditions within a basin of a thermal treatment system during surgical procedures and facilitating control of thermal treatment of said basin and sterile medium contained therein in response to said detected conditions, said device comprising:

a surgical drape to cover and substantially conform to said basin to serve as a drape container for said sterile medium; and a sensing device including a plurality of conductors with at least two of said conductors disposed on a sterile drape surface within said drape container and responsive to contact with said sterile medium to indicate conditions of said drape container, wherein said drape includes a pouch to house said at least two conductors.

50. The device of claim 49, wherein said pouch is attached to said drape via intermittent seams.

51. A method of detecting conditions during surgical procedures within a container formed within a thermal treatment system basin by a surgical drape to contain sterile medium and controlling thermal treatment of said drape container in response to said detected conditions, said method comprising:

(a) receiving said surgical drape over said thermal treatment system to cover and substantially conform to said basin to serve as a drape container for said sterile medium, wherein said drape includes a sensing device to detect drape container conditions including sterility of said drape, wherein said sensing device includes a status device and a plurality of conductors responsive to contact with said sterile medium to indicate conditions of said drape container, and wherein said status device includes a plurality of states with the state of said status device indicating said sterility of said drape;

(b) determining occurrence of said drape container conditions from signals from said sensing device and controlling said thermal treatment system to thermally treat said basin in accordance with said determined drape container conditions.

52. The method of claim 51, wherein at least two conductors are disposed on a sterile drape surface and step (b) further includes:

(b.1) determining occurrence of drape container conditions from signals from said plurality of conductors.

53. The method of claim 52, wherein said status device is coupled to at least one of said conductors, and step (b) further includes:

(b.2) determining occurrence of said drape container conditions based on the state of said status device indicating sterility of said drape.

54. The method of claim 51, wherein said status device includes a fuse.

55. The method of claim 52, wherein said sensing device includes a strip with said plurality of conductors disposed thereon and a connector, and step (a) further includes:

(a.1) coupling said drape to said thermal treatment system via said connector.

56. The method of claim 55, wherein said connector includes said status device and at least a portion of said plurality of conductors.

57. The method of claim 55, wherein said strip includes a temperature sensor coupled to at least one of said conductors, and step (b.1) further includes:

(b.1.1) measuring temperature of said sterile medium.

58. The method of claim 51, wherein step (b) further includes:

(b.1) detecting a change in a sterile medium amount within said drape container, wherein said sensing device includes at least one of a weight sensor to measure a change in weight of said basin indicating said change in said sterile medium amount, an optical sensor to detect an implement within said basin altering said sterile medium amount, a proximity sensor to detect said implement within said basin altering said sterile medium amount, a Hall effect sensor to detect said implement within said basin altering said sterile medium amount and an RFID reader to detect an RFID label disposed on said implement to detect said implement within said basin altering said sterile medium amount.

59. The method of claim 51, wherein said sensing device includes a connector with a processor, and step (b) further includes:

(b.1) providing signals from said processor to said thermal treatment system to indicate at least one of said status and said drape container conditions.

60. The method of claim 56, wherein said thermal treatment system includes a receptacle and step (a.1) further includes:

(a.1.1) receiving said connector in said receptacle to couple said drape to said thermal treatment system.

61. The method of claim 51, wherein a first state of said status device enables an electrical path and indicates a sterile drape, and a second state of said status device disables said electrical path and indicates prior use of that drape, and step (b) further includes:

(b.1) providing a status signal on said electrical path and detecting characteristics of said electrical path to determine said state of said status device and ascertain said sterility of said drape.

62. The method of claim 61, wherein step (b.1) further includes:

(b.1.1) determining a random time interval and providing said status signal and determining said status device state in response to expiration of that time interval.

63. The method of claim 61, wherein step (b) further includes:

(b.2) disabling said electrical path by controlling said status device to enter said second state to indicate use of said drape in response to detection of characteristics indicating an enabled electrical path.

64. The method of claim 63, wherein step (b) further includes:

(b.3) providing said status signal on said electrical path to said status device and verifying placement of the status device in said second state, wherein detection of said status device in said second state indicates a sterile drape and detection of said status device in said first state indicates a used drape utilizing a conductive member with said status device in said second state.

65. The method of claim 51, wherein step (b) further includes:

(b.1) actuating at least one of a visual and an audio indicator to indicate said determined occurrence of said drape container conditions.

66. The method of claim 51, wherein said drape container conditions further include at least one of a leak and the presence of said sterile medium within said drape container, and step (b) further includes:

(b.1) disabling said thermal treatment system in response to determining at least one of the presence of a leak, absence of said sterile medium within said drape container and said status indicating a non-sterile drape.

67. The method of claim 51 further including:

(c) collecting information relating to a surgical procedure and generating a report including said collected information.

68. The method of claim 67, wherein step (c) further includes:

(c.1) providing information for said report via at least one of a bar code scanner and an RFID reader.

69. The method of claim 67 further including:

(d) printing a hardcopy of said report.

70. The method of claim 69, wherein step (d) further includes:

(d.1) enabling printing of said report after system power down for a predetermined interval.

71. The method of claim 67 further including:

(d) establishing communications and transferring information with another device.

72. The method of claim 71, wherein step (d) further includes:

(d.1) generating said report in electronic form and transmitting said report to said other devise.

73. The method of claim 51, wherein said drape container conditions further include at least one of a leak and the presence of said sterile medium within said drape container, and step (b) further includes:

(b.1) enabling said thermal treatment system in response to determining the presence of said sterile medium and absence of a leak within said drape container.

74. The method of claim 52, wherein at least one circuit path is coupled to said at least two conductors to receive signals from said sensing device to determine said drape container conditions, and step (b.1) further includes:

(b.1.1) providing power signals to at least one conductor in an oscillating fashion to prevent said sterile medium from attaining a charge.

75. The method of claim 52, wherein said drape includes a pouch to house said at least two conductors.

76. The method of claim 75, wherein said pouch is attached to said drape via intermittent seams.

* * * * *